Figure 1A:
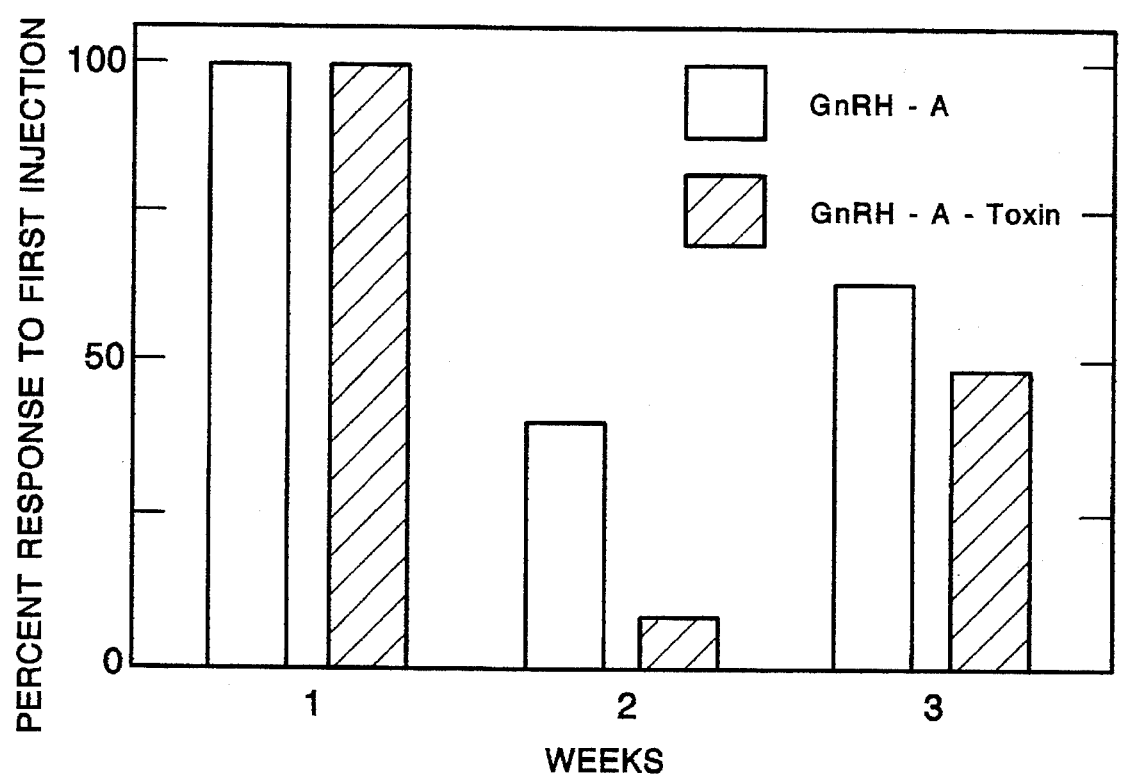

United States Patent [19]

Nett et al.

[11] Patent Number: 5,631,229
[45] Date of Patent: *May 20, 1997

[54] METHOD FOR INACTIVATING GONADOTROPHS

[75] Inventors: Torrance M. Nett, Ft. Collins; Leonard M. Glode, Aurora, both of Colo.

[73] Assignee: Colorado State University Research Foundation, Fort Colllins, Colo.

[*] Notice: The term of this patent shall not extend beyond the expiration date of Pat. No. 5,378,688.

[21] Appl. No.: 88,434

[22] Filed: Jul. 7, 1993

Related U.S. Application Data

[60] Division of Ser. No. 837,639, Feb. 14, 1992, Pat. No. 5,378,688, which is a continuation-in-part of Ser. No. 314,653, Feb. 23, 1989, abandoned.

[51] Int. Cl.$^6$ .................. A61K 38/00; A61K 38/02; C07K 5/00; C07K 7/00
[52] U.S. Cl. .................. 514/15; 514/12; 514/14; 530/313; 530/324; 530/328; 530/345
[58] Field of Search .................. 514/12, 15, 14; 530/324, 313, 328, 345, 398

[56] References Cited

U.S. PATENT DOCUMENTS

| | | | |
|---|---|---|---|
| 4,081,533 | 3/1978 | Cheesman | 424/177 |
| 4,201,770 | 5/1980 | Stevens | 424/177 |
| 4,302,386 | 11/1981 | Stevens | 260/112 |
| 4,400,376 | 8/1983 | Sanderson | 424/88 |
| 4,444,759 | 4/1984 | Rivier et al. | 424/177 |
| 4,526,716 | 7/1985 | Stevens | 260/112.5 |
| 4,691,006 | 9/1987 | Stevens | 530/324 |
| 4,767,842 | 8/1988 | Stevens | 530/324 |
| 4,863,857 | 9/1989 | Blalock et al. | 435/68 |
| 5,378,688 | 1/1995 | Nett et al. | 514/15 |

OTHER PUBLICATIONS

Bacha et al., "Organ-Specific Binding of a Thyrotropin-Releasing Hormone-Diphtheria Toxin Complex after Intravenous Administration to Rats", pp. 1072–1076, 1983, *Endocrinology*, vol. 113.

Bacha et al., "Systemic Toxicity of Diphtheria Toxin-Related Fragments (CRM26, CRM45), a Hormone-Toxin Hybrid Protein (TRH-CRM45), and Ricin A$^1$ (42234)", pp. 131–138, 1986, *Proc. Soc. Exp. Biol. Med.*, vol. 181.

Bacha et al., "Thyrotropin-Releasing Hormone-Diphtheria Toxin-Related Polypeptide Conjugates; Potential Role of the Hydrophobic Domain in Toxin Entry", pp. 1565–1570, 1983, *J. Biol. Chem.*, vol. 258, Feb.

Bourdon et al., "The Potential of Monoclonal Antibodies as Carriers of Radiation and Drugs for mmunodetection and Therapy of Brain Tumors", pp. 79–101, 1984, *Prog. exp. Tumor Res.*, vol. 28.

Cawley et al., "Epidermal Growth Factor–Toxin A Chain Conjugates: EGF–Ricin A is a Potent Toxin While EGF–Diphtheria Fragment A is Nontoxic", pp. 563–570, 1980, *Cell*, vol. 22, Nov.

Chang et al., "Artificial Hybrid Protein Containing a Toxic Protein Fragment and a Cell Membrane Receptor–Binding Moiety in a Disulfide Conjugate", pp. 1515–1522, 1977, *J. Biol. Chem.*, vol. 252, Feb.

Chaudhary et al., "Activity of a Recombinant Fusion Protein Between Transforming Growth Factor Type α and Pseudomonas Toxin", pp. 4538–4542, 1987, *Proc. Natl. Acad. Sci. USA*, vol. 84, Jul.

Colombatti et al., "Cloned Fragment of Diphtheria Toxin Linked to T Cell–Specific Antibody Identifies Regions of B Chain Active in Cell Entry", pp. 3030–3035, 1986, *J. Biol. Chem.*, vol. 261, Mar.

Greenfield et al., "Mutations in Diphteria Toxin Separate Binding from Entry and Amplify Immunotoxin Selectivity", pp. 536–539, 1987, *Science*, vol. 238, Oct.

Meyers et al., "Specific Chemical Cleavage of Diphtheria Toxin With Hydroxylamine", pp. 17122–17127, 1988, *J. Biol. Chem.*, vol. 263, No. 32 Nov.

Murphy et al., "Genetic Construction, Expression, and Melanoma–Selective Cytotoxicity of a Diphtheria Toxin–Related α–Melanocyte–Stimulating Hormone Fusion Protein", pp. 8258–8262, 1986, *Proc. Natl. Acad. Sci. USA*, vol. 83, Nov.

Myers, "Hybrid Toxins: An Approach to Cell Specific Toxicity", 1987, Dissertation submitted to the Division of Animal Science and the Graduate School of the University of Wyoming, Laramie, Wyoming.

Myers D. A., et al., "Protein–Peptide Conjugation By A Two–Phase Reaction", p. 343, 1985, *Biochem J.*, 227:1.

Oeltmann et al., "A Hybrid Protein Containing the Toxic Subunit of Ricin and the Cell–Specific Subunit of Human Chorionic Gonadotropin", pp. 1028–1032, 1979, *J. Biol. Chem.*, vol. 4, Feb.

Oeltmann, "Synthesis and In Vitro Activity of a Hormone–Diphtheria Toxin Fragment of a Hybrid", pp. 430–435, 1985, *Biochem. Biophys. Res. Commun.*, vol. 133, Dec.

Pastan et al., "Immunotoxins", pp. 641–648, 1986, *Cell*, vol. 47, Dec.

Pineda M.H. et al., "Atrophy of Rabbit Testes Associated with Production of Antiserum to Bovine Luteinizing Hormone", pp. 665–668, 1967, Proc. Soc. Exp. Bio. Med., vol. 125, No. 3, Jul.

Quadri S.K. et al., "Inhibition of Spermatogenesis and Ovulation in Rabbits With Antiovine LH Rabbit Serum", pp. 809–814, 1966, Proc. Soc. Exp. Bio. Med., vol. 123.

(List continued on next page.)

*Primary Examiner*—Avis M. Davenport
*Attorney, Agent, or Firm*—Sheridan Ross & McIntosh

[57] ABSTRACT

Certain toxic compounds (T) such as, for example, compounds based upon diphtheria toxin, ricin toxin, pseudomonas exotoxin, α-amanitin, pokeweed antiviral protein (PAP), ribosome inhibiting proteins, especially the ribosome inhibiting proteins of barley, wheat, corn, rye, gelonin and abrin, as well as certain cytotoxic chemicals such as, for example, melphalan and daunomycin can be conjugated to certain analogs of gonadotropin-releasing hormone to form a class of compounds which, when injected into an animal, destroy the gonadotrophs of the animal's anterior pituitary gland. Hence such compounds may be used to sterilize such animals and/or to treat certain sex hormone related diseases.

27 Claims, 8 Drawing Sheets

OTHER PUBLICATIONS

Schwartz et al., "A New Cytotoxin Specific for the Target Cells of Corticotropin–Releasing Factor", pp. 1454–1460, 1987, *Endocrinology*, vol. 121.

Singh et al., "Controlled Release of LHRH–DT From Bioerodible Hydrogel Microspheres", pp. R5–R8, 1976, *International Journal of Pharmacology*.

Tallgat M. et al., "Impairment of Spermatogenesis And Libido Through Antibodies to Luteinizing Hormone", pp. 113–118, 1971, Fertility and Sterility, vol. 22, No. 2, Feb.

Vitetta et al., "Redesigning Nature's Poisons to Create Anti–Tumor Reagents", pp. 1098–1104, 1987, *Science*, vol. 238, Nov.

Youle et al., "Immunotoxins Show Rapid Entry of Diphtheria Toxin but not Ricin via the T3 Antigen", pp. 93–98, 1986, *J. Immunol.*, vol. 136, Jan.

BARLEY HEMITOXIN

Fig. 2B

Effect of 2 - Iminothiolane Conjugation on Barley Toxin Activity

□ – – Unconjugated
○ —— 0.76 Molar Ratio
△ – – – 1.44 Molar Ratio

Fig. 4

METHOD FOR INACTIVATING GONADOTROPHS

RELATED APPLICATIONS

This patent application is a divisional of U.S. patent application Ser. No. 07/837,639, filed Feb. 14, 1992, now U.S. Pat. No. 5,378,688 entitled "GnRH Analogs for Destroying Gonadotrophs" which is a continuation-in-part of U.S. patent application Ser. No. 314,653, filed Feb. 23, 1989, now abandoned and also entitled "GnRH Analogs for Destroying Gonadotrophs."

FIELD OF THE INVENTION

The present invention generally relates to methods for sterilizing animals and to methods for medically treating certain sex hormone related diseases such as, for example, cancer of the breast or prostate. More particularly, this invention relates to sterilization and medical treatment by means of chemical attack upon the pituitary gland.

BACKGROUND OF THE INVENTION

Considerable interest exists with respect to the subject of sterilization of animals. This is especially true of those concerned with veterinary medicine and animal husbandry, particularly as they relate to the subject of sterilization of domestic animals such as dogs, cats, cattle, sheep, horses, pigs, and the like. Various methods have been developed over the years to accomplish sterilization. For example, with respect to male cattle, the most widely used procedure for eliminating problems of sexual or aggressive behavior is sterilization through surgical castration. This is done in various ways, e.g., crushing the spermatic cord, retaining the testes in the inguinal ring, or use of a rubber band, placed around the neck of the scrotum, to cause sloughing off of the scrotum and testes. However most of these "mechanical" castration methods have proven to be undesirable in one respect or another; for example they (1) are traumatic, (2) introduce the danger of anesthesia, (3) are apt to produce infection, and (4) require trained personnel. Moreover, all such mechanical castration methods result in complete abolition of the testes and this of course implies complete removal of the anabolic effects of any steroids which are produced by the testes and which act as stimuli to growth and protein deposition.

These drawbacks have caused consideration of various alternative sterilization techniques such as the use of chemical sterilization agents. However, the use of chemical sterilization agents has its own set of advantages and disadvantages. On the positive side, chemical sterilization eliminates the stress and danger associated with mechanical castration. Chemical sterilization also has the added advantage of allowing for retention of certain anabolic effects resulting from a continued presence of low levels of circulating testosterone. This is especially valuable in the case of animals raised for human consumption since circulating testosterone promotes growth, efficiency of feed conversion and protein deposition. Unfortunately, there are several disadvantages associated with chemical sterilization. For example chemical sterilization is often temporary rather than permanent; it also sometimes produces extremely severe, and even fatal, side effects.

Many of these chemical sterilization methods have been aimed at regulation of luteinizing hormone produced at various stages of an animal's sexual development. For example, with respect to cattle it has been established that in the case of the infantile calf, luteinizing hormone is rarely discharged and testicular production of androgens is at low levels. On the other hand, in a prepubertal calf, or an adult bull, discharges of luteinizing hormone from the anterior pituitary occur more frequently and the testes produce considerably larger amounts of testosterone and other steroids. It is thought that these conditions result from the following factors: (1) decreases in the concentration of estradiol receptors in the hypothalamus, (2) concomitant increases in the concentration of estradiol receptors in the anterior pituitary, and (3) increases the number of gonadotropin-releasing hormone (GnRH) receptors in the anterior pituitary. This increase in GnRH receptors is generally regarded as a prerequisite for an animal to pass from the infantile stage to the prepubertal and mature stages of endocrine development. Hence, based upon these understandings of the hypothalamic-pituitary-testicular axis, several chemical methods have been proposed to modify given animals, e.g., a bull calf, in such a way that it never enters puberty, but still receives stimuli for growth and protein deposition through the anabolic effects of steroids produced by modified testes. In any event, most of the chemicals proposed for such sterilization purposes are hormones or hormone analogs. For example U.S. Pat. No. 4,444,759 teaches the use of a class of peptides analogous to GnRH (i.e., gonadotropin-releasing hormone, and particularly luteinizing hormone-releasing hormone) are capable of inhibiting release of gonadotropins by the pituitary gland and thereby inhibiting release of the steroidal hormones, estradiol, progesterone and testosterone. It should also be noted that the terms "GnRH" (gonadotropin-releasing hormone) and "LHRH" (luteinizing hormone-releasing hormone) are sometimes used interchangeably in the literature. For the purposes of describing the prior art both terms may be employed; however, for the purposes conveying the teachings of our patent disclosure, applicants prefer the term GnRH and will use it in describing their compounds.

Be that as it may, some prior art chemical sterilization procedures are specifically adopted to alter luteinizing hormone secretion before the animal has attained the age of puberty. This is not surprising since the role of luteinizing hormone in sexual maturation is well known. Luteinizing hormone is a gonadotropic hormone found in the anterior lobe of the pituitary gland and, in male animals, it is known to stimulate the interstitial cells of the testes to secrete testosterone (see generally, The Merck Index, 8th edition, p. 560 (1968), Encyclopedia of Chemical Technology, Vol. 7, pp. 487–488 (1951)).

One approach has been to use certain chemicals to produce antibodies in an animal which exhibit cross-reactivity with the gonadotropins produced by the animal's pituitary gland. It is generally thought that with such early antigenic stimulation, formation of antibodies is more continuously stimulated by the release of endogenous hormones and that early immunization with such luteinizing hormone deters the maturation of the gonads and adnexal glands. This, in turn, is thought to inhibit spermatogenesis at the spermatogonial level. For example, U.S. Pat. No. 4,691,006 teaches injection of a compound having an amino acid sequence of at least 20 units for purposes of eliciting formation of antibodies which exhibit cross-reactivity with the gonadotropins produced by the animal's pituitary. With early antigenic stimulation of this kind, the formation of such antibodies is more continuously stimulated by release of endogenous hormones. Early immunization with such luteinizing hormone also deters the maturation of the gonads and adnexal glands. However, the art has also recognized that early immunization of this kind may tend to make the interstitial tissues fibroblastic. It has also been found that such early stimulation of the immunologic system leads to development of a high titered antiserum to luteinizing hormone which remains at relatively high levels. Nonetheless, periodic boosters of such compounds are often necessary even for adult animals sterilized before puberty in order to maintain high levels of the neutralizing antibodies.

Similarly, luteinizing hormone has been administered to animals after they have attained the age of puberty in order to atrophy their reproductive organs and to cause a decrease in libido (see generally, M. Tallau and K. A. Laurence, Fertility and Sterility, Vol. 22, No. 2, February 1971, pp. 113–118, M. H. Pineda, D. C. Lueker, L. C. Faulkner and M. L. Hopwood, Proceedings of the Society for Experimental Biology and Medicine, Vol. 125, No. 3, July 1967, pp. 665–668, and S. K. Quadri, L. H. Harbers, and H. G. Spies, Proc. Soc. Exp. Biol. Med., Vol. 123, pp. 809–814 (1966). Such treatments also impair spermatogenesis in noncastrated adult male animals by interruption of the spermatogenic cycle.

Other chemical sterilization agents have been specifically designed for use on female animals. For example, it is well known that certain antigens will produce an antiserum against a requisite estrogen. This is accomplished by first making an antigen and then injecting said antigen into an animal for purposes of antiserum production. The animal is then bled to recover the antiserum. Any female animal of the same species as the host animal may then be injected with the antiserum at the proper time prior to ovulation and the injected antiserum will cause temporary sterilization of that animal.

Other methods of chemical sterilization have been based upon direct chemical attack upon certain cells of the pituitary itself (as opposed to chemical attacks upon the hormone products of such cells) with a view toward permanently destroying such cells. Again, this approach is suggested by the fact that follicle stimulating hormone (FSH) and luteinizing hormone (LH) (sometimes referred to as gonadotropins or gonadotropic hormones) are released by the pituitary gland to regulate functioning of the gonads to produce testosterone in the testes and progesterone and estrogen in the ovaries. They also regulate the production and maturation of gametes.

Several chemical agents have been proposed for such purposes. However, it has been found that most chemical agents which are in fact capable of destroying the gonadotrophs of an animal's anterior pituitary gland also tend to produce extremely toxic side effects which can severely weaken, and sometimes kill, the treated animal. Hence, with respect to the general subject of chemical sterilization, it can be said that any chemical capable of producing sterilization without, or with minimal, toxic side effects would be of great value in the fields of animal husbandry, veterinary medicine and wildlife control.

To date, perhaps the closest concepts and/or compounds to those described in this patent disclosure are found in a publication by Myers, D. A., Murdock, W. J. and Villemez, C. L., entitled Protein-Peptide Conjugation By A Two-Phase Reaction: *Biochem. J.*, 227:1 pg. 343 (1985). This reference teaches a sterilization procedure employing a GnRH analog comparable to that utilized by applicant in one of his more preferred GnRH/toxin conjugate compounds, namely one based upon a GnRH/diphtheria toxin conjugate. However, there are some very pronounced differences in the toxin portions of the respective molecules. These differences reside in the fact that different parts or portions of the diphtheria toxin are employed in the respective resulting compounds. More specifically, the conjugate reported by Myers et al. utilized only the toxin domain of the diphtheria toxin molecule while applicant's diphtheria toxins are characterized by their possession of the membrane translocation domain of this toxin as well as the toxic domain. The details and significance of these molecular differences are important to this patent disclosure and will be discussed at greater length in subsequent parts of this patent disclosure.

However, before leaving this discussion of the GnRH/diphtheria conjugate aspect of the prior art, it also should be noted that in addition to the article by Myers et al. noted above, Myers, on another occasion, published additional information concerning his diphtheria toxin-GnRH analog conjugate. This was done in his Ph.D. thesis at the University of Wyoming in 1987, entitled: "Hybrid toxins: An approach to cell specific toxicity." This thesis contains basically the same information as the above-noted 1985 publication, but—of course—in much greater detail. For example, the thesis includes further information on the biological activity of the Myers conjugate. A second part of this thesis addresses modifications of Myers' diphtheria toxin in a manner similar to that described above, but using further information published by Colombatti et al. in the Journal of Biological Chemistry 261:3030 (1986).

Another reference of possible interest in this regard was recently published in the INTERNATIONAL JOURNAL OF PHARMACOLOGY 76: R5–R8 by Singh et al. entitled "Controlled release of LHRH-DT from bioerodible hydrogel microspheres." Generally speaking, it teaches that a natural GnRH/diphtheria toxin can be used as a vaccine. In this case the LHRH-DT molecule induces production of antibodies to GnRH which then serve to inactivate endogenous LHRH in the circulation. Without the endogenous LHRH, there is no stimulation of the anterior pituitary gland to secrete LH and the gonads will cease functioning. However, as the antibody titers fall, endogenous GnRH will again stimulate the anterior pituitary gland, LH secretion and gonadal function will return. Here again, those skilled in this art will appreciate that this is an entirely different approach from the "direct chemical attack on the pituitary gland" approach taught in this patent disclosure. That is to say that—unlike Singh's antibody production approach—applicant's conjugate will not generate antibodies to GnRH and no neutralization of endogenous GnRH will occur. Instead, with applicant's approach, the cells in the anterior pituitary gland which are activated by GnRH will be destroyed by direct chemical attack thereon. Moreover, this attack results in permanent, rather than temporary sterility.

However, before going on to these details, it also should be noted that knowledge of the above noted sex hormone functions has produced several advances in the field of human medicine as well. For example, the potential for achieving chemical castration (rather than "surgical" castration) with certain luteinizing hormone-releasing hormone (LHRH) analogs has been reported (see for example, Javadpour, N., Luteinizing Hormone-Releasing Hormone (LHRH) in Disseminated Prostatic Cancer; 1M, Vol. 9, No. 11, November 1988). Table I below gives the structure of LHRH and the structure of certain analogs (e.g., Goserelin, Leuprolide, Buserelin and Nafarelin) of LHRH which are capable of temporarily suppressing luteinizing hormone secretion and thereby suppressing the gonads. As a consequence, these LHRH analogs have come to be regarded as a promising new class of agents for the treatment of various host-dependent diseases, especially prostatic cancer. In referring to Table I, it first should be noted that LHRH has a decapeptide structure and that substitution of certain amino acids in the sixth and tenth positions of the LHRH produce analogs which render agonists that are up to 100 times more potent than the parent LHRH compound (hence these compounds are often referred to as "superagonists"). The structures of LHRH and the most commonly known LHRH superagonists are listed below.

STRUCTURES OF LHRH AND SOME SUPERAGONISTS
(Superagonists have substitutions at positions 6 and 10)

LHRH:

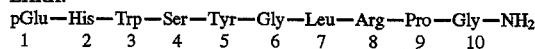

pGlu—His—Trp—Ser—Tyr—Gly—Leu—Arg—Pro—Gly—$NH_2$
 1    2    3    4    5    6    7    8    9    10

SUPERAGONISTS:

| Name | Subs. at 6 | Subs. at 10 | Terminator |
| --- | --- | --- | --- |
| Goserelin: | D-Ser(tBu) | AzaGly | Amide |
| Leuprolide: | D-Leu | des-Gly | Ethylamide |
| Buserelin: | D-Ser(tBu) | des-Gly | Ethylamide |
| Nafarelin: | D-2-NaphthylAla | None | Amide |

While these compounds represent the most promising means for palliative therapy because of their relative lack of side effects, they are particularly expensive and must be administered repeatedly. Even the newest formulations utilizing polymer encapsulated drug or other depot forms will require at least monthly administration. Improved depot forms also are presently in development, but they too are likely to be equally expensive and they too will probably require monthly administration. In response to these many drawbacks, applicants have developed a class of compounds which is capable of producing safe, inexpensive, chemical castration as an alternative to surgical castration. Such drugs also greatly simplify therapy of the generally elderly patients with prostate cancer, and could eliminate the need for surgical castration (still preferred by many urologists) as well as provide a medical alternative to oophorectomy in females with advanced breast cancer. Moreover, as a model system, the ability to eliminate pituitary gonadotrophs in vivo, which are regulated by GnRH receptors in response to ligand stimulation in a predictable fashion, is a highly appealing first step toward the more complex use of toxins conjugated to antibodies to eliminate tumor targets. Hence, use of applicants' compounds generally will fall into two major areas of use. The first is sterilization of mammals of all types; the second is chemical castration of mammals in general, and human beings in particular, for purposes of treating breast or prostate cancer by ablating those pituitary cells, namely gonadotrophs, responsible for LH secretion.

SUMMARY OF THE INVENTION

The present invention provides a group of GnRH/toxin conjugate compounds and processes for using them to sterilize mammals (animals and humans) and/or for treating certain sex hormone related diseases such as cancer of the prostate or cancer of the breast. The active parts of these compounds or agents may be referred to as "toxic compounds", ("T") or "toxins" for the purposes of this patent disclosure without changing the intended scope of the herein described compounds and/or processes. In any event, the most effective, and hence most preferred, of these toxin compounds will include: diphtheria toxin, ricin toxin, abrin toxin, pseudomonas exotoxin, shiga toxin, α-amanitin, pokeweed antiviral protein (PAP), ribosome inhibiting proteins (RIP), especially the ribosome inhibiting proteins of barley, wheat, flax, corn, rye, gelonin, abrin, modeccin and certain cytotoxic chemicals such as, for example, melphalan, methotrexate, nitrogen mustard, doxorubicin and daunomycin. All of these toxins are characterized by their inability, in their own right, to chemically attack the gonadotropin-secreting cells of the anterior pituitary gland as well as by their concomitant ability to chemically attack gonadotropin-secreting cells when conjugated with GnRH molecules (and GnRH analogue molecules) according to the teachings of this patent disclosure.

Some of these toxins (e.g., bacterial toxins and certain plant toxins) can be characterized by whether or not a "whole" molecule of a given toxin is employed. For the purposes of this patent disclosure the term "whole" may be taken to mean that the molecule has at least a toxic domain, a translocational domain and a cell binding domain. If, however, one or more of these domains are removed from a "whole" toxin molecule, then the resulting molecule will be characterized as a "modified" toxin or "modified" molecule of that toxin. TABLE I below gives some representative "whole" and "modified" toxins. Some of these toxin types (e.g., bacterial and plant toxins) also can be further characterized by their possession of so-called "A-chain" and "B-chain" groups in their molecular structures. It also should be noted that the toxic domain is often referred to as the "A-chain" portion of the toxin molecule while the toxic domain, translocation domain and cell-binding domain are often collectively referred to as the "whole" toxin or the A-chain plus the B-chain molecules. For example, such further classifications could be made according to the attributes, categories and molecular sizes noted in TABLE I below (wherein the letters A and B represent the presence of A-chains or B-chains and the letter K designates the symbol ("kilodalton" used to designate molecular sizes of such molecules):

TABLE I

Single Chain Toxins

Pokeweed antiviral protein

Gelonin ribosome-inhibiting protein (RIP)

Wheat RIP

Barley RIP

Corn RIP

Rye RIP

Flax RIP

Bacterial Toxins

Diphtheria toxin (whole) having a toxic domain, a translocation domain and a cell-binding domain=62K Diphtheria toxin (modified) having a toxic domain and a translocation domain=45K Pseudomonas exotoxin (whole) having a toxic domain, a translocation domain and a cell-binding domain=66K Pseudomonas exotoxin (modified) having a toxic domain and a translocation domain=40K Shiga toxin (whole) having a toxic domain, a translocation domain and a cell binding domain=68K Shiga toxin (modified) having a toxic domain=30K

Plant Toxins

Ricin A+B (whole)=62K

Ricin A=30K

Abrin A+B=62K

Abrin A=30K
Modeccin A+B=56K
Modeccin A=26K

Small Chemical Toxins

Melphalan
Methotrexate
Nitrogen Mustard
Daunomycin
Doxorubicin

Applicants have also found that of all the possible toxin molecules noted above, the bacterial and plant toxins having both a toxic domain and a translocation domain (which may also be referred to as B-chain "parts", "shortened B-chain, amino acid sequences", etc.), but not a cell-binding domain are the most effective—and hence the most preferred—conjugate compounds for applicant's sterilization purposes. The procedures by which cell-binding domains can be deleted are of course well known to this art and need not be discussed in any great detail.

Moreover, in considering the general subject of transmembrane transport proteins, as they relate to this invention, applicants would also point out that there are a number of viral proteins, for example, which function in ways similar to the "translocation domain" functions of diphtheria toxin, ricin, and of Pseudomonas toxin. These include the Sendai virus HN and F glycoproteins, and the Adenovirus penton proteins along with similar fusogenic proteins of Semliki Forest virus. Also, lipophilic polylysines, such as poly(1-lysine) conjugated to glutarylphosphatidylethanolamine can function in this way. Consequently, those skilled in the art will appreciate that the transmembrane transport of applicants' conjugates can be enhanced by inclusion of any such fusogenic moieties into our GnRH-toxin conjugates.

However, regardless of such concerns for the presence, identity, and/or size of B-chains in certain toxin molecules, applicants have found that all of the herein described sterilization agents can be most effectively delivered to the pituitary gland if they are chemically conjugated with various peptide hormone molecules such as certain analogs of gonadotropin-releasing hormone, GnRH. Again, this conjugation is necessary because, for the most part, the above toxins, by themselves, are not capable of binding with cell membranes in general. That is to say that applicants have found that it is only when a GnRH analog of the type described herein is linked to a toxin of the types noted above does that toxin become capable of binding to cell membranes, and then only to those cells whose membranes contain receptors for GnRH (i.e., gonadotrophs in the anterior pituitary gland). Other less preferred, but still operative peptide hormone molecules (other than applicant's preferred gonadotropin-releasing hormone analogues) to which the herein disclosed toxins could be so conjugated for applicant's sterilization purposes include: human chorionic gonadotropin, equine chorionic gonadotropin, luteinizing hormone and follicle-stimulating hormone.

At this point, it should again be emphasized that for the purposes of this patent disclosure, the term gonadotropin-releasing hormone will usually be abbreviated as "GnRH" and that, for the most part, certain hereinafter described analogs of GnRH are generally more effective carrier peptide hormone molecules for the practice of this invention than the fundamental or parent GnRH molecule. In their most generalized sense, these analogs will be abbreviated as "GnRH-A", with the "A" designating that the resulting compound is an analog, "A" of the fundamental GnRH molecule. Again, any general toxin compound which is conjugated with a GnRH-A molecule will be abbreviated by the letter "T" for toxin. Thus, the abbreviation for a generalized conjugate of a GnRH-A analog and a toxin will be "GnRH-A-T".

In the case of GnRH-A carrier peptide molecules, the linking or coupling of the GnRH-A molecule and the T molecule is preferably carried out at the 6 position of the GnRH-A molecule. This modification may include use of a linkage using a heterobifunctional reagent "Y" which will be described in much more detail in subsequent portions of this patent disclosure. That is to say that the most preferable technique for production of the resulting GnRH-A-T conjugate molecule will involve modification of the 6 position of the fundamental GnRH molecule. In other words, amino acid substitutions at the 6 position of the fundamental GnRH molecule will yield analogs with particularly high affinities for GnRH receptors on cells of the pituitary gland and thereby providing an improved means for introducing the toxin into the targeted cells.

The most preferred amino acids for substitution at the 6-position will include lysine, D-lysine, aspartic acid, D-aspartic acid, glutamic acid, D-glutamic acid, cysteine, D-cysteine, ornithine, D-ornithine, tyrosine, D-tyrosine as well as other amino acids having suitable side-Chain functional groups such as, for example, amino groups, carboxylic groups, hydroxyl groups or sulfhydryl groups. Similarly the 10 position of the fundamental GnRH molecule can be modified to produce other analog variations useful for applicant's purposes. The substituents most preferred for this purpose will include Gly-$NH_2$, ethylamide and AzA-Gly-$NH_2$.

Heterobifunctional reagent Y is, most preferably, used to link a GnRH-A group or moiety to a toxic group or moiety T. Most preferably such toxic groups T and their associated GnRH-A carrier peptide molecules will be covalently linked by a linking or coupling agent selected from the group consisting of 2-iminothiolane, N-succinimidyl-3-(2-pyridyldithio) proprionate (SPDP), 4-succinimidyloxycarbonyl-α-(2-pyridyldithio)-toluene (SMPT), m-maleimidobenzoyl-N-hydroxysuccinimide ester (MBS), N-succinimidyl(4-iodoacetyl)aminobenzoate (SIAB), succinimidyl 4-(p-maleimidophenyl)butyrate (SMPB), 1-ethyl-3-(3-dimethylaminopropyl)carbodiimide (EDC), bis-diazobenzidine and glutaraldehyde.

Given all of these structural concerns, a generalized chemical structural diagram of an amino acid sequence of a GnRH molecule and of a group of highly preferred resulting GnRH-A-T carrier peptide molecules for the practice of this invention could be depicted as follows:

$$\text{pyroGlu—His—Trp—Ser—Tyr—X—Leu—Arg—Pro—Z} \quad \text{(Eq. I)}$$
$$1 \quad 2 \quad 3 \quad 4 \quad 5 \quad 6 \quad 7 \quad 8 \quad 9 \quad 10$$
$$|$$
$$Y$$
$$|$$
$$T$$

wherein X is an amino acid, Y is a linking group, Z is a chemical substituent selected from the group consisting of Gly-$NH_2$, ethylamide and Aza-Gly-$NH_2$ and T is a toxin group selected from the group consisting of the plant toxins: ricin, modeccin, abrin, pokeweed anti-viral protein, α-amanitin, gelonin ribosome inhibiting protein ("RIP") barley RIP, wheat RIP, corn RIP, rye RIP and flax RIP; the bacterial toxins selected from the group consisting of: of diphtheria toxin, pseudomonas exotoxin and shiga toxin (and especially those bacterial toxins having a toxic domain and a translocation domain) and the chemical toxins selected from the group consisting of: melphalan, methotrexate, nitrogen mustard, doxorubicin and daunomycin.

Those skilled in this art will appreciate that some specific compounds falling within the above generalized structure are often referred to as "D-Lys$^6$-GnRH." That is, in normal peptide nomenclature, the reference to D-Lys$^6$ before the GnPH indicates that the normal 6-position amino acid group of the GnRH molecule (i.e., a "Gly" group), has been replaced by lysine. Thus, the X, i.e., the 6-position X amino acid would in fact be lysine. Hence, the most general GnRH-A amino acid sequence could be depicted as follows:

(Eq. II)

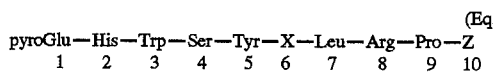

pyroGlu—His—Trp—Ser—Tyr—X—Leu—Arg—Pro—Z
   1      2     3     4    5    6    7     8    9    10

That is to say that, applicant's molecules will be further characterized by having a generalized amino acid in the X (or 6) position. Preferably, this amino acid will be selected from the group consisting of: lysine, D-lysine, ornithine, D-ornithine, glutamic acid, D-glutamic acid, aspartic acid, D-aspartic acid, cysteine, D-cysteine, tyrosine and D-tyrosine.

Within the possibilities implicit in the general structure, a particularly preferred GnRH analog would be:

(Eq. III)

pyroGlu-His-Trp-Ser-Tyr-D-Lys-Leu-Arg-Pro-ethylamide

This molecule also could be referred to as [D-Lys$^6$-des-Gly$^{10}$]-GnRH-ethylamide and, regardless of nomenclature, it represents one of applicant's most preferred GnRH-A molecules.

The presence of the Y component of the most general structure (i.e., Equation I) is optional—but highly preferred. Again, if used, such Y groups are most preferably selected from the group consisting of: 2-iminothiolane, N-succinimidyl-3-(2-pyridyldithio) proprionate (SPDP), 4-succinimidyloxycarbonyl-α-(2-pyridyldithio)-toluene (SMPT), m-maleimidobenzoyl-N-hydroxysuccinimide ester (MBS), N-succinimidyl(4-iodoacetyl)aminobenzoate (SIAB), succinimidyl 4-(p-maleimidophenyl)butyrate (SMPB), 1-ethyl-3-(3-dimethylaminopropyl)carbodiimide (EDC), bis-diazobenzidine and glutaraldehyde.

The most preferred forms of these compounds will have an amino group, a carboxylic group and/or a sulfhydryl group, to aid in the Y group's performance of this GnRH-A to T linking function. In other words the T group most preferably will be attached to a GnRH-A molecule by means of an amino, carboxylic or sulfhydral group of 2-iminothiolane, N-succinimidyl-3-(2-pyridyldithio) proprionate (SPDP), 4-succinimidyloxycarbonyl-α-(2-pyridyldithio)-toluene (SMPT), m-maleimidobenzoyl-N-hydroxysuccinimide ester (MBS), N-succinimidyl(4-iodoacetyl)aminobenzoate (SIAB), succinimidyl 4-(p-maleimidophenyl)butyrate (SMPB), 1-ethyl-3-(3-dimethylaminopropyl)carbodiimide (EDC), bis-diazobenzidine and glutaraldehyde. Similarly, the Y group most preferably will be attached to the X group at the site of an amino group, a carboxylic group, a sulfhydryl group or a hydroxyl group of whatever amino acid group is employed at the 6-position of applicant's GnRH-A molecule.

As previously noted, the T group represents a toxin group which, first and foremost, is capable of chemically attacking the gonadotrophs of the pituitary gland when conjugated to the carrier peptide (GnRH-A) molecules described in this patent disclosure. Again, as seen in TABLE I, certain toxins T such as the bacterial toxins and plant toxins such as ricin, abrin and modeccin, can be composed of a toxic domain (also referred to as an A-chain), a translocation domain and a cell-binding domain (the latter two domains are sometimes referred to as the B-chain) and that applicants believe that, in general, use of toxins having a toxic domain plus a translocation domain, but not a cell-binding domain, will give more effective results than use of toxins having only a toxic domain (A-chain) only or a toxic domain, translocation domain and cell-binding domain (also referred to as whole toxin or A-chain plus B-chain). The ribosome-inhibiting proteins (RIP) also will be effective toxins, but here again, only after conjugating them to a GnRH analog. That is to say that by themselves, they are not toxic since they do not contain a cell membrane binding domain. However, if conjugated to one of applicant's GnRH analogs, the resulting conjugate molecule can interact with GnRH receptors and gain entry into the pituitary cell, thereby preventing protein synthesis and ultimately causing the desired effect— cell death. The RIPs of barley, corn, wheat, rye and flax will be especially useful for this purpose. Pokeweed antiviral protein is similar in nature to the RIPs noted above and hence can also be employed as the toxin T. The bacterial toxins, diphtheria toxin, pseudomonas exotoxin and shiga toxin are especially preferred. Again, these bacterial toxins are originally comprised of a toxic domain, a translocation domain and a cell-binding domain, but applicants have found that in general those having their toxic domain plus their translocation domain are generally more effective than those bacterial toxin having only a toxic domain or those comprised of the whole molecule. Chemical toxins selected from the group consisting of melphalan, methotrexate, nitrogen mustard, doxorubicin and daunomycin are particularly preferred. Obviously, A-chain and B-chain considerations will not be applicable to "chemical" toxins because they are not made up of amino acid groups such as those found in bacterial or plant toxins.

It should, however, also be noted that regardless of whether the toxin T is comprised of an A-chain, an A-chain plus a portion of a B-chain, or a chemical molecule which does not contain an amino acid sequence, it is preferably attached to the GnRH portion of the overall conjugate molecule via a linking Y compound selected from the group consisting of: 2-iminothiolane, N-succinimidyl-3-(2-pyridyldithio) proprionate (SPDP), 4-succinimidyloxycarbonyl-α-methyl-α-(2-pyridyldithio)-toluene (SMPT), m-maleimidoacetyl)aminobenzoate (SIAB), succinimidyl 4-(p-maleimidophenyl)butyrate (SMPB), 1-ethyl-3-(3-dimethylaminopropyl)carbodiimide (EDC), bis-diazobenzidine and/or glutaraldehyde.

It should again be emphasized that one particularly important aspect of the herein disclosed invention is based upon applicant's finding that those appropriate (i.e., bacterial or plant) toxin moieties having both an A-chain and at least a portion of a B-chain, but not all of the B-chain, in the overall GnRH/toxin conjugate molecules are especially well suited to the herein described sterilization functions. This preference for the presence of a portion of a given toxin's B-chain in the overall conjugate molecule is important to this patent disclosure for several reasons. First, applicant's B-chain-containing compounds have proven to be generally much more effective sterilization agents than those amino acid containing toxins having only an "A-chain" portion. Moreover, such amino acid containing toxins also tend to be less toxic in their side effects.

This difference also serves to distinguish applicant's invention from those other sterilization methods using GnRH molecules in their own right or from those employing other GnRH/toxin conjugate compounds. For example, the previously noted GnRH/diphtheria toxin used in the process reported by Myers et al. utilized only the A-chain portion of the diphtheria toxin molecule. That is to say that diphtheria toxin is a 62 kilodalton protein, composed of a 21 kilodalton A chain and a 37 kilodalton B chain linked together by disulfide bonds. Myers et al, in effect, confirmed that an A-chain, diphtheria toxin can serve to inhibit protein synthesis in a cell by catalyzing the ADP-ribosylation of a cell constituent known as "elongation factor 2." Again, in the absence of protein synthesis, a cell cannot function and eventually dies.

This follows from the fact that a cell's elongation factor 2 is located in its cytoplasm, and a toxin such as diphtheria toxin must first gain entry into the cytoplasm in order for its toxicity to be manifested. Thus, the most preferred forms of toxins for the practice of this invention (e.g., use of diphtheria toxin in applicant's resulting GnRH-A-T conjugates) will have a toxin molecule which includes the toxic domain (for cytotoxicity) and the translocation domain that increases the ability of the overall molecule to cross cell membranes. That is to say that this translocation domain "portion" serves to greatly assists entry of the toxic domain portion of the toxin into a cell's cytoplasm and thus increases the potency of the resulting conjugate as a sterilization agent.

Applicant has, however, found that the presence of the translocation domain of a toxin such as diphtheria toxin greatly enhances the sterilization efficacy and/or nontoxicity of GnRH-A-T conjugates of the type disclosed in this patent application. Again, use of an entire toxin molecule is not preferred for applicant's purposes. That is to say that in those cases where an overall toxin molecule contains a toxic domain, a translocation domain and a cell-binding domain, applicant prefers to delete the cell-binding domain.

For example, a diphtheria B chain has two parts, a translocation domain and a cell-binding domain. These two portions are a carboxyl terminal of 8 kilodaltons which contains a cell surface binding domain that permits diphtheria toxin to attach to nearly all mammalian cells to which it is exposed and an amino terminal of 21 kilodaltons which contains several hydrophobic regions that can insert into a membrane at a low pH. The cell-binding domain of the diphtheria's B-chain is preferably cleaved away.

As previously noted, in some of the most preferred conjugate molecules, applicant has provided a diphtheria toxin portion comprised of a toxic domain and a translocation domain and additionally comprising a "spacer" group which most preferably ends in a cysteine residue. This arrangement has the advantage of providing a free sulfhydryl group that can be used to attach the toxin molecule to the GnRH analog in such a way as to minimize interference with the desired enzymatic activity (i.e., performance of the toxicity function of the toxic domain).

Again, applicant has discovered that the analogue of the GnRH molecule having the following structure:

pyroGlu-His-Trp-Ser-Tyr-D-Lys-Leu-Arg-Pro-ethylamide is particularly efficacious for conjugation and delivery of a diphtheria toxin comprised of an A-chain and a part or fragment of the diphtheria toxin molecule's B-chain amino acid sequence. As previously noted, this molecule could be referred to as the [D-Lys$^6$-des-Gly$^{10}$]-GnRH-ethylamide analogue of the GnRH molecule. Regardless of nomenclature, applicant has found this to be the most effective (and, hence, the most preferred) GnRH analogue/ diphtheria toxin conjugate for applicant's sterilization methods. And, as in the more general cases noted in the previous discussion of the nature of the 6 position "X" group of the more general molecular structures, lysine, D-lysine, ornithine, D-ornithine, glutamic acid, D-glutamic acid, aspartic acid, D-aspartic acid, cysteine, D-cysteine, tyrosine and D-tyrosine could each be substituted in the amino acid #6 position of this most preferred [D-Lys$^6$-des-Gly$^{10}$]-GnRH ethylamide/diphtheria molecule. However, it also should be noted that the analogs resulting from these changes at the 6 position are generally somewhat less preferred, but still useful, for applicant's general process.

The resulting conjugates are specifically targeted to the gonadotropin-secreting cells of the anterior pituitary gland. Indeed they are the only cells to which the gonadotropin-releasing hormone portion of applicant's conjugates will bind. Hence, the toxic compounds, bound to an analog of gonadotropin-releasing hormone, serve to permanently destroy a subpopulation of the anterior pituitary cells and thereby eliminate the gland's ability to secrete gonadotropins. Applicant has termed this mechanism "direct chemical attack" to contrast it with the use of certain GnRH molecules to elicit an immune response to the gonadotropin products of the pituitary. This direct chemical attack upon the pituitary gland, in turn, causes the animal's gonads to atrophy and lose their ability to function for reproductive purposes. In other words, without functioning gonadotrophs, an animal is not able to secrete luteinizing hormone (LH) and follicle-stimulating hormone (FSH) and thus is rendered sterile. Applicants have postulated that the compounds of this patent disclosure inhibit synthesis of LH, and presumably other proteins made by gonadotrophs, because they tend to inhibit all protein synthesis once these compounds gain entry into the pituitary cells.

Consequently, these compounds have great potential utility in human medicine as well as in veterinary medicine. This follows from the fact that there are several important biological reasons for employing castration and antifertility drugs in humans. For example, breast and prostate cancers are but two examples of sex steroid-dependent tumors which respond to such hormonal manipulation. At present, the only reliable way to inhibit steroid-dependent tumor growth is through administration of counter-regulatory hormones (e.g., DES in prostate cancer), sex-steroid hormone binding inhibitors (e.g., tamoxifen in breast cancer) or surgical castration. Thus the potential medical uses of such chemical castration compounds are vast and varied. For example, prostate cancer remains an important cause of cancer deaths and represents the second leading cancer of males. The present palliative treatment for advanced prostate cancer cases involves reduction of serum testosterone/DHT levels through use of surgical castration. It should also be noted that for purposes of disease and/or fertility control, especially in humans, it may be desirable to use applicants' compounds to ablate pituitary gonadotrophs in conjunction with other modes of treatment. For example, it is anticipated that chronic administration of progestins and estrogens to females and androgens to males might be necessary to prevent loss of secondary sex characteristics, behavior and osteoporosis. However, through judicious use of the herein disclosed compounds, especially in combination with appropriately administered sex steroids, desirable antifertility effects can be achieved. Another area of application in human medicine is treatment of endometriosis. This condition, which produces painful growth of endometrial tissue in the female peritoneum and pelvis also responds to inhibition of sex steroid synthesis. Those skilled in this art will also appreciate that the herein disclosed compounds could be used to partially reduce sex-steroid secretions, and thus reduce or eliminate certain hormone related behavior problems while retaining improved growth stimulation.

The dose/time adjustments associated with the use of these compounds can vary considerably; however, these compounds are preferably administered by injection into a mammal in concentrations of from about 0.1 to about 10 milligrams per kilogram of the mammal's body weight. Sterilization may be accomplished with as few as one injection; but multiple treatments (e.g., based upon concentrations of from about 0.03 milligrams once every 4 days to about 1 milligram per kilogram of body weight for 20 days) are alternative sterilization schemes. Furthermore, as sterilization agents, the compounds of this patent disclosure can be used before or after puberty. They too are especially useful in those areas of animal husbandry where the anabolic benefits of non-surgical sterilization techniques can contribute to meat production and/or quality. In one preferred embodiment of this invention the compounds of this invention are administered to male cattle between the ages of about 8 weeks and 20 weeks at least once and in a concentration of from about 0.1 to about 10 milligrams per kilogram of the animal's body weight.

The toxic moieties T of the herein disclosed compounds are obtainable from both natural and synthetic sources. For example, pokeweed antiviral protein can be isolated from leaves of pokeweed plants and purified by gel filtration chromatography. It can then be, by way of example, conjugated to D-$Lys^6$-des$Gly^{10}$]-GnRH-ethylamide via the amino group on the lysine and through a sulfhydryl group introduced into the pokeweed antiviral protein by a heterobifunctional reagent. In any event, one of the chief advantages of these compounds is their ability to produce permanent sterilization without strong toxic side effects. Hence these compounds may be used on mammals such as human beings, domestic animals, pets or wild animals. Moreover, they can be administered as a single injection which can induce permanent and irreversible sterility in both male and female mammals. However, an alternative approach to achieve sterilization is through multiple injections at lower dosages than those employed in a single treatment or by slow release implants (i.e., biodegradable formulations).

Applicants also have postulated that the "B-chain" portion of their toxic moieties are important not only for binding to cell surfaces, but for trans-membrane translocation of their A-chain. This was particularly demonstrated for the A-chain of Diphtheria toxin, Ricin and Pseudomonas exotoxin. To this end, applicants prepared conjugates of GnRH-A to A and B chains of Diphtheria toxin as well as to a modified A-B chain which was genetically engineered to eliminate the carboxy terminal binding portion of the B-chain. These conjugates were shown to bind to pituitary cell GnRH receptors. They also were found to possess enhanced toxicity over A-chain conjugates based on improved trans-membrane transport characteristics. Given this, those skilled in the art will appreciate that numerous genetic and chemical modifications of B-chains should allow further exploitation of this approach. That is to say that, by such methods, it is possible to generate a whole series of conjugates that can be characterized as GnRH-A-A/B, GnRH-A-A, GnRH-A-A plus GnRH-B, all of which could enhance the findings described herein by simultaneous delivery of membrane active B-chains with the herein described GnRH-A-T conjugates.

DESCRIPTION OF DRAWINGS

FIGS. 1A and 1B respectively depict the results of GnRH induced secretion of LH based upon a single injection of a GnRH-A-T compound and the results of GnRH induced secretion of LH based upon 4 injections of a GnRH-A-T compound.

FIGS. 2A and 2B indicate inactivation of certain grain hemitoxins (wheat hemitoxin and barley hemitoxin) by SPDP conjugation.

FIG. 3 depicts the results of a SDS-PAGE analysis of carbodiimide conjugated hemitoxins.

FIG. 4 shows the inhibition of 2-iminothiolane-conjugated barley hemitoxin.

FIG. 4A shows SDS-PAGE analysis of barley hemitoxin after conjugation to [D-$Lys^6$, des-$Gly^{10}$]-GnRH-ethylamide using 2-iminothiolane.

FIG. 5 shows binding curves indicating the ability of [D-$Lys^6$, des-$Gly^{10}$]-GnRH-ethylamide toxin conjugates to bind to pituitary receptors.

DESCRIPTION OF THE PREFERRED EMBODIMENTS

One of the chief objects of this invention is to provide a class of compounds which will allow safe, inexpensive, chemical castration. As such, applicants' compounds represent an alternative to surgical castration as well as to surgery for treatment of diseases such as breast cancer or certain sex hormone related prostate cancers. In order to better define this class of compounds, Applicants conducted studies on various linking technologies as they apply to numerous toxin candidates. These studies resulted in the herein disclosed group of conjugate compounds. In general these compounds display good gonadotroph membrane binding characteristics along with retention of toxin activity.

In general, the sterilization activity of the compounds of this patent disclosure was tested in receptor binding assays (to be sure a given conjugate was still capable of interacting with the GnRH receptor cells of the pituitary), in a cell-free translation system (to insure that the toxic protein maintained its toxicity), in cell culture systems (to determine if a given toxic conjugate is capable of inhibiting synthesis of LH), and in test animals (to determine if sterility was induced). For example, one of the more effective of these sterilization agents was a [D-$Lys^6$-des-$Gly^{10}$]-GnRH-ethylamide which was conjugated to pokeweed antiviral protein using carbodiimide as the "linkage" group Y between the carrier protein molecule and the toxin moiety.

Again, a distinct advantage of each of the sterilization agents of this invention, and pokeweed antiviral protein in particular, is that they have an extremely limited ability to enter cells in an animal's body unless they are first conjugated to a carrier such as gonadotropin-releasing hormone. Such conjugation was accomplished in several ways. By way of example, pokeweed antiviral protein can be conjugated to a [D-$Lys^6$, des-$Gly^{10}$]-GnRH-ethylamide molecule via the ϵ-amino group on the D-lysine to a sulfhydryl group on the pokeweed antiviral protein.

By way of further information, applicants found that this type of linkage reduces the ability of the [D-$Lys^6$, des-$Gly^{10}$] -GnRH-ethylamide to bind to the GnRH receptor by 99%. In addition, the conjugation procedure reduces the toxicity of the pokeweed antiviral protein by 99.5 in a cell-free translation system. However, despite large reductions in activity of both the GnRH analog and the sterilization agent by this particular conjugation procedure, some activity of each was maintained. The activity of this conjugate was also tested in a pituitary cell culture system. In this system, pituitary cells were incubated with the sterilization agent conjugated to

[D-Lys$^6$, des-Gly$^{10}$]-GnRH-ethylamide for 16 hours. After incubation, the sterilization agents were removed from the incubation media by extensive washing and the cells were then cultured for an additional 24 hours. The increase in total LH, i.e., that present in the media plus that in the cells during the 24 hour period, represents the ability of the treated cells to synthesize LH. Using this system, it was established that these toxic conjugates can completely inhibit synthesis of LH by the cultured cells. Thus, by this method, it was established that the compounds of this patent disclosure can inhibit synthesis of LH and presumably other proteins made by gonadotrophs since this class of compounds has the ability to inhibit all protein synthesis once they gain entry into a cell.

Figure 1B:
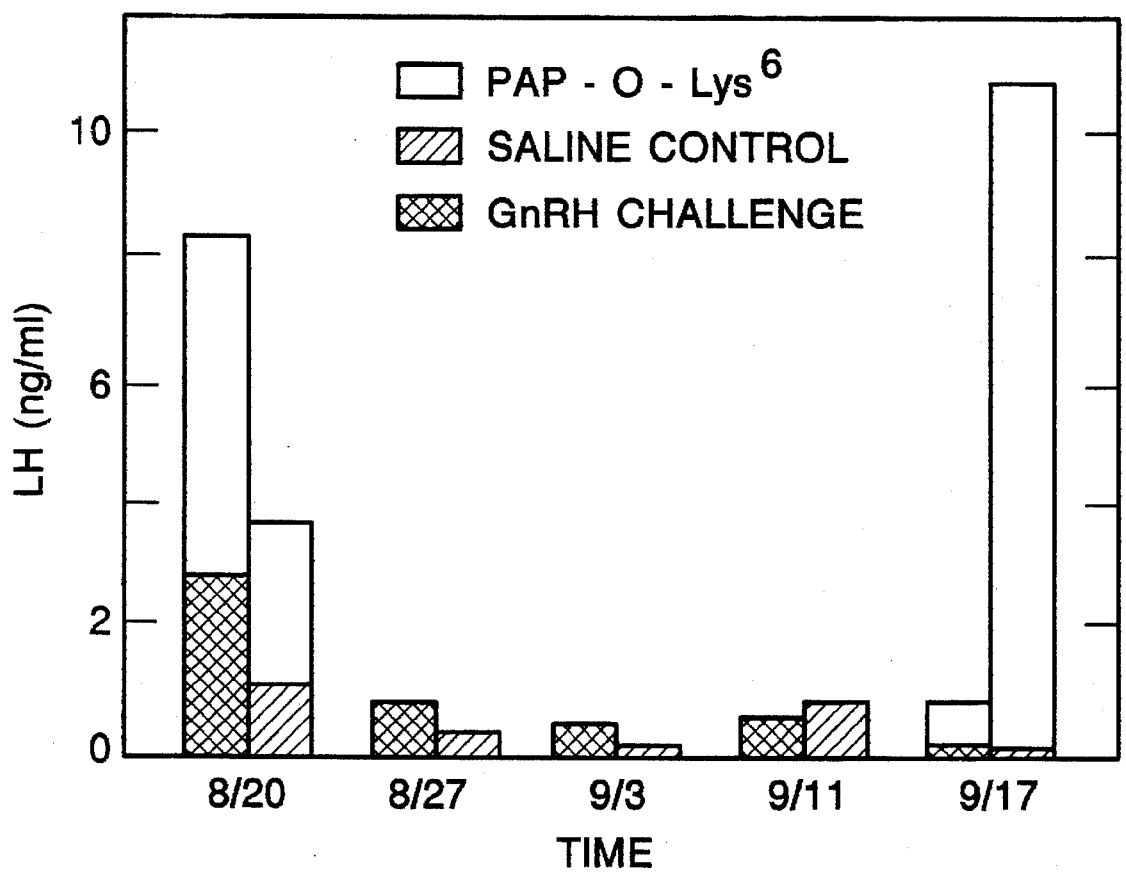

Applicants also tested these compounds using an in vivo model. The test system initially chosen was the ovariectomized female rat. The parameter examined was GnRH induced secretion of LH. The results of such an experiment with rats are shown in FIG. 1A. It indicates that a single injection of a toxic conjugate (i.e., GnRH-A-T) wherein the toxic moiety (T) pokeweed antiviral protein and the GnRH-A moiety was [D-Lys$^6$, des-Gly$^{10}$]-GnRH-ethylamide. During week 1, this compound induced secretion of LH equivalent to that of GnRH-A alone. This indicated that the sterilization agent conjugate was binding to the GnRH receptor in vivo. During week 2, release of LH was reduced by 50% in the GnRH-A treated group (controls), but by >90% in the GnRH-A-T group. By the third week, the release of LH in the GnRH-A-T group had returned to the same level as that observed in the control animals. This indicated that a single treatment with the sterilization agent conjugate was probably not sufficient to completely kill the gonadotrophs in vivo. It might however be the basis for a temporary sterilization. Based upon this finding, a second experiment was conducted to examine the effect of 4 injections of a pokeweed antiviral sterilization conjugate at 3-day intervals on the ability of ovariectomized rats to release LH. In this experiment, the rats were unable to release LH in response to GnRH stimulation one month after initiation of the treatment (FIG. 1B). These data strongly indicate the ability of these conjugates to permanently inhibit reproduction in intact male and female animals.

In another set of experiments, intact rats were given 4 injections of GnRH-A-T compounds, again wherein the toxic moiety T was selected from pokeweed antiviral protein, ricin A chain, and ribosome inhibiting proteins, of certain grains (again, those of wheat, corn, barley and rye,) at 3-day intervals and their subsequent reproductive capacity was compared to rats treated with only the respective toxin T or to that of untreated rats. In this experiment, treatment of male rats with only the toxin T did not reduce their fertility compared to controls (percentage of females that became pregnant was 100%). However, fertility was greatly reduced in those males that were treated with a GnRH-A-T agent such as, for example [D-Lys$^6$-des-Gly$^{10}$]-GnRH-ethylamide conjugated to pokeweed antiviral protein, i.e., only 50% of the females exposed to males became pregnant. Moreover, fertility did not appear to increase with time after treatment. Histological examination of the testes of these rats indicated that most of the seminiferous tubules were devoid of sperm. However, 10% of the tubules appeared to still be producing sperm and probably accounted for the pregnancies observed. The weight of the testes was reduced by nearly 50% and did not recover within 6 months after the end of treatment. Thus, the effects of the treatment appeared to be permanent and dose related. Female rats treated with the toxic conjugate were sterile and remained so for at least 4 months (i.e., about 30 reproductive cycles) after the end of treatment. Most important is the fact that none of the rats treated with the toxic conjugate appeared to have any side effects.

Exemplary Chemical Experimental Methods

1. Synthesis of [D-Lys$^6$, des-Gly$^{10}$]-GnRH-ethylamide. Synthesis of this analogue was accomplished using the solid phase method on hydroxymethyl resin and cleavage from the resin by ethyl amine, yielding the ethylamide. Following HF cleavage of protecting groups from side chains the peptide was purified by countercurrent distribution, purity of the peptide was assured by TLC, paper electrophoresis, and amino acid analysis of the acid hydrolysate.

2. Applicants also produced a caproic acid derivative (134.91 mg) and the lysosomal hydrolase sensitive tetrapeptide spacer Leu-Ala-Leu-Ala-D Lys$^6$ (16.25 mg).

3. Conjugation of [D-Lys$^6$, des-Gly$^{10}$]-GnRH-ethylamide to toxins using SPDP. Applicants endeavored to construct toxic conjugates of [D-Lys$^6$, des-Gly$^{10}$]-GnRH-ethylamide with the ricin A-chain. At the time these studies were initiated, Ricin A-chain was commercially available, but applicants found it to be both expensive and very unstable to temperature changes or conjugation procedures. Construction of an effective hemitoxin [D-Lys$^6$, des-Gly$^{10}$]-GnRH-ethylamide conjugate requires coupling of hemitoxin to hormone via a protein cross-linking reagent that does not block either the enzymetic activity of the hemitoxin or the binding specificity of the hormone. Therefore, applicants investigated a number of different hemitoxins in addition to ricin A and pokeweed antiviral protein and a number of different conjugation techniques. This work was largely directed at purification of certain plant hemitoxins, i.e., ribosomal inhibitory proteins, ("RIP"), a relatively recently recognized group of proteins which share the ability to enzymically inactivate mammalian ribosomes. Such toxins are potentially promising as alternatives to the more familiar A-chains of, for example, ricin in that they do not require separation from the cell-binding B-chains. The bi-functional coupling reagent most commonly used for this purpose is N-succinimidyl 3-(2-pyridyldithio) propionate (SPDP). This compound forms covalent linkages to either free amino or sulfhydryl groups on proteins, but SPDP normally is attached to amino groups in hemitoxins, partly because many hemitoxins do not contain sylfhydryls that are available for coupling.

Initial experiments examined the reaction of SPDP with both the wheat and barley hemitoxins at various SPDP: hemitoxin ratios. The reactions were carried out at pH 9 for 30 minutes at 23° C. at a protein concentration of 0.6 mg/ml. After 30 minutes a 20-fold molar excess (over SPDP) of lysine was added to react with free SPDP and the hemitoxins diluted and assayed for inhibition of polyphenylalanine synthesis on Ehrlich ascites cell ribosomes. The results are presented in FIG. 2.

Figure 2A:
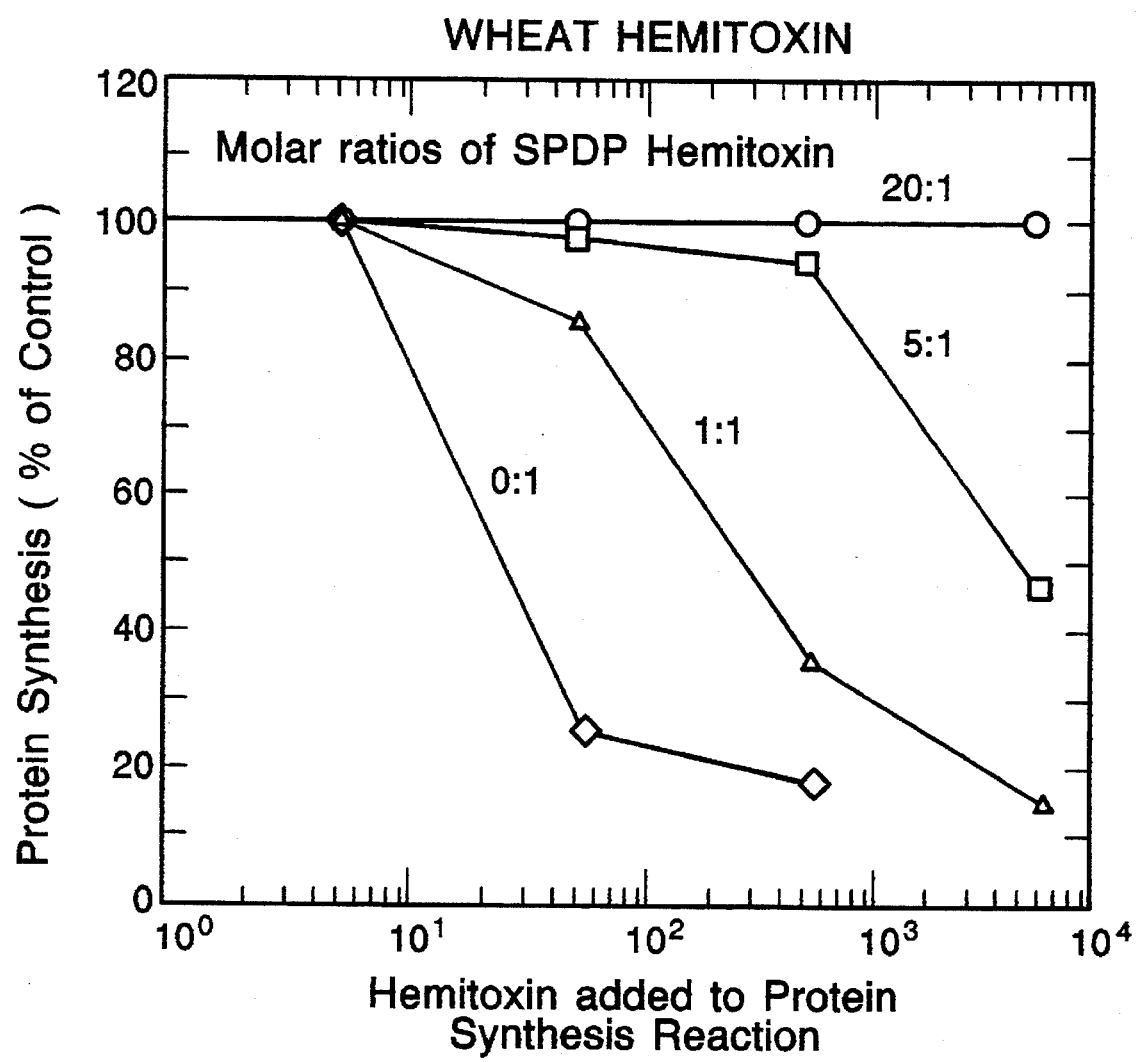
Figure 2B:
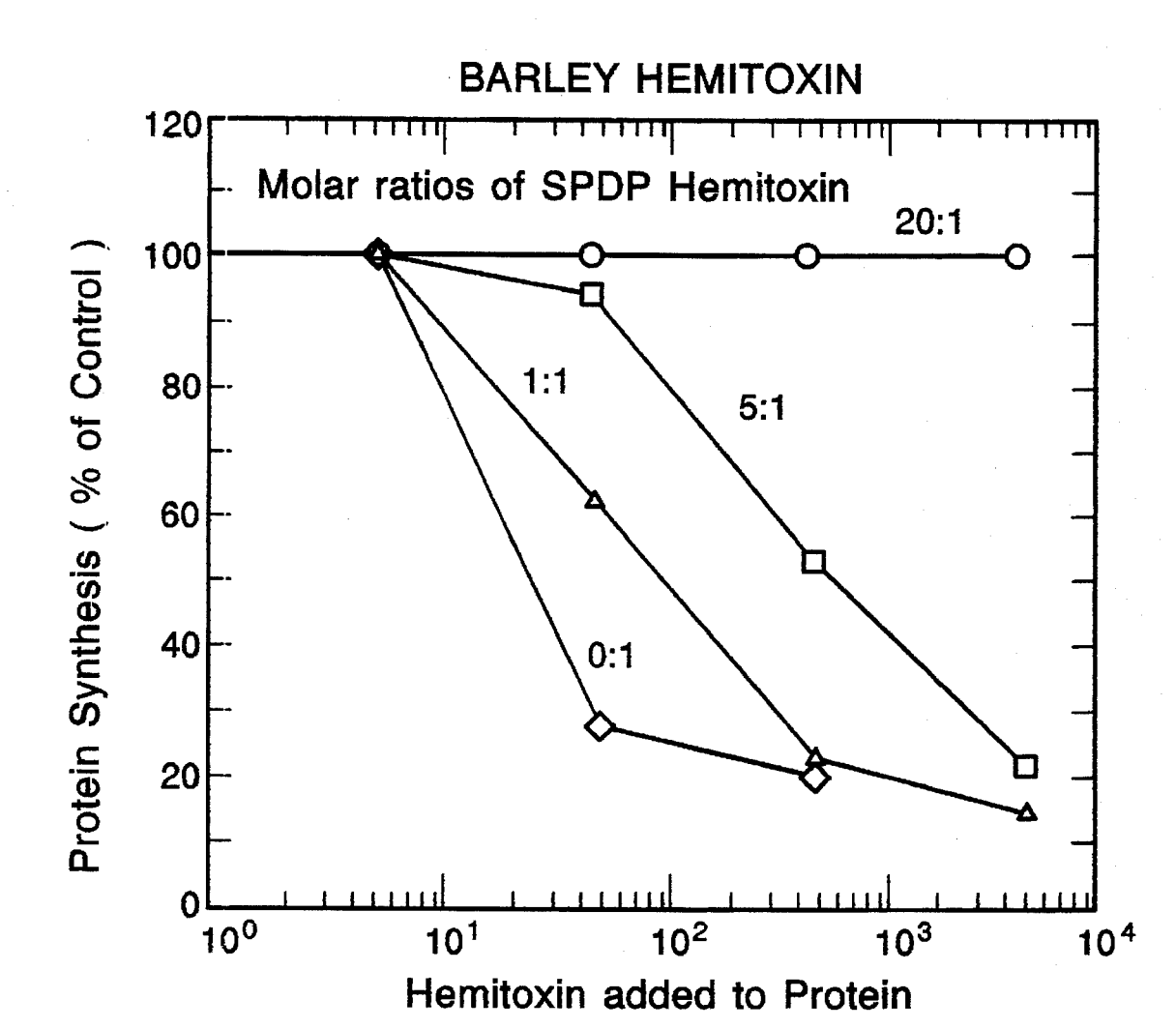

FIG. 2 is intended to show inactivation of certain grain hemitoxins by SPDP conjugation. It indicates that even 1:1 ratios of SPDP to hemitoxin result in significant inactivation which is complete at a 20:1 ratio. A commonly used 2-3 fold ratio would result in >95% inactivation. Applicants' study was expanded to include hemitoxins from corn and pokeweed. Reactions were carried out in phosphate buffers at neutral and acidic pH's in anticipation that under acidic conditions differences in pKa of lysine amino groups or conformational changes in some of the proteins might protect enzymic activity. However, in all conditions and with all 4 hemitoxin proteins, significant inactivation occurred and as quantitative activity measurements of hemitoxins were rather imprecise; hence applicants were unable to conclude that residual activity was not from unreacted hemitoxin. Moreover, these particular experiments indicated SPDP would be unsuitable as a coupling reagent for preparing many GnRH-A-T conjugates.

4. Conjugation of [D-Lys$^6$, des-Gly$^{10}$]-GnRH-ethylamide to toxins using Carbodiimide. Applicants examined the ability of the water soluble coupling reagent, carbodiimide linkages in this class of compounds. Although carbodiimide has been used successfully for coupling polypeptide hormones to proteins, applicants are unaware of any studies reporting its use in preparing toxin-protein conjugates. However, its use turned out to be attractive since it couples through carboxyl groups on the hemitoxin rather than amino groups. It should also be noted that applicants' synthetic GnRH analogs are blocked at the carboxyl and amino termini, thus leaving, for example, D-lys$^6$ amine as the only reactive moiety. Use of large molar ratios of GnRH favors reaction of the hemitoxin to the analog rather than to itself.

Figure 3:
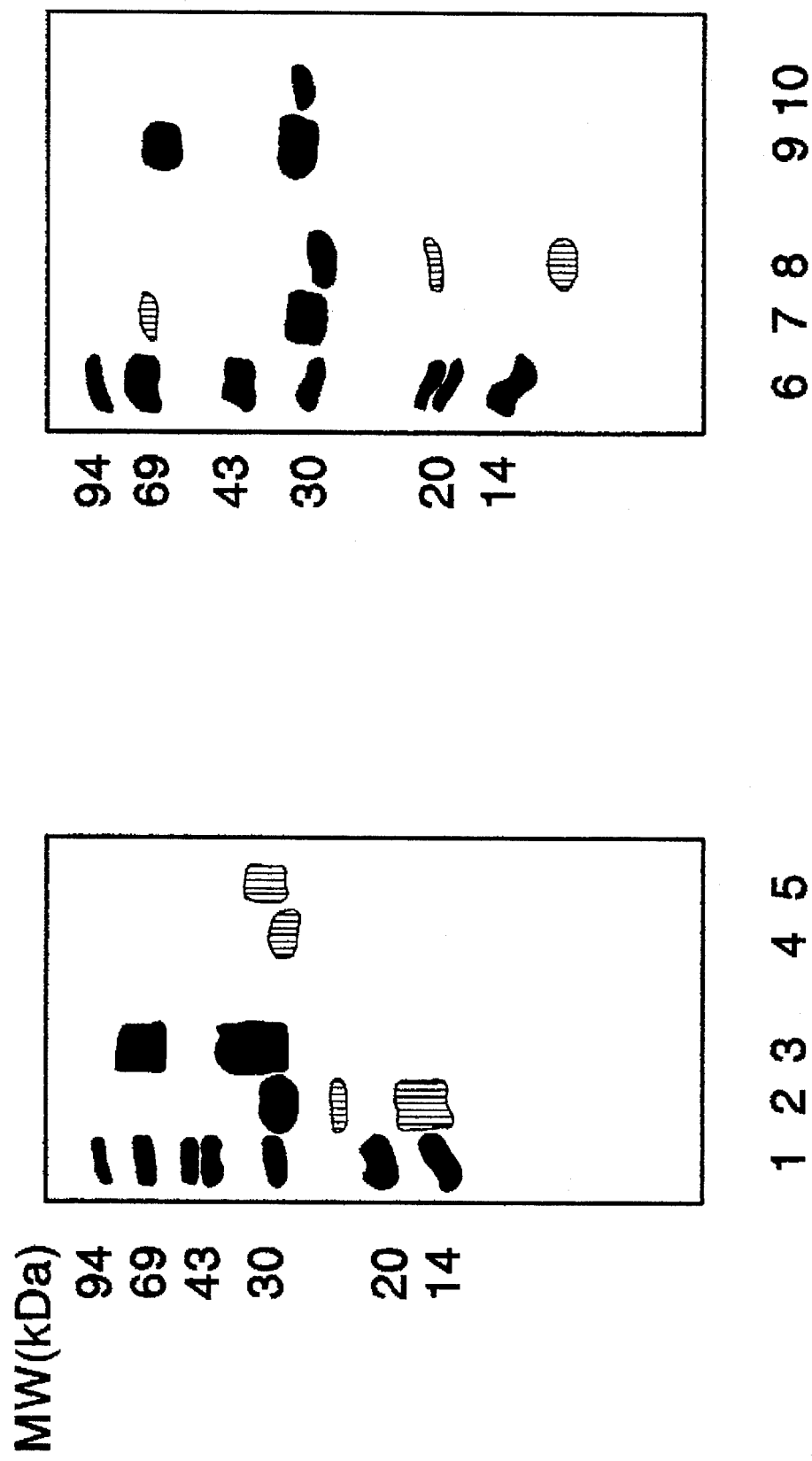

FIG. 3 shows the successful results of this approach. It represents a SDS-PAGE analysis of carbodiimide conjugated hemitoxins. In order to carry out these experiments, a 30:1 molar ratio of [D-Lys$^6$, des-Gly$^{10}$]-GnRH-ethylamide to hemitoxin was reacted with 1-ethyl-3-(3-dimethylaminopropyl) carbodiimide (EDAC) in water at 23° C. for 30 minutes and the reaction mixture passed through a Bio-Gel P6 column to desalt the product. Protein containing fractions were assayed for residual activity (see text) and the reaction products examined by SDS polyacrylamide gel electrophoresis. Lanes 1, and 6 are standards; lane 2, barley; lane 3, barley-GnRH; Lane 4, pokeweed; lane 5, pokeweed-GnRH; lane 7, rye-GnRH; lane 8, rye; lane 9, gelonin-GnRH; lane 10, gelonin. Conjugation in each case resulted in a 32 kDa product which was distinct from the 30 kDa hemitoxin alone, and which (by enzyme assay) retained 10% of the original activity. Hemitoxins from barley, rye, wheat and the unrelated pokeweed and gelonin hemitoxins have each been successfully conjugated in this fashion and all retain about 10% of original toxicity in ascites ribosomal assay. Biologic studies with these conjugates were then completed in the manner hereinafter described.

5. Conjugation of [D-Lys$^6$, des-Gly$^{10}$]-GnRH-ethylamide to toxins using 2-iminothiolane. Although 2-iminothiolane, like SPDP, reacts with free amino groups on proteins, it does not affect the activity of gelonin or PAP. Applicants have hypothesized that perhaps the reason 2-iminothiolane differs from SPDP in this regard is that it reacts with a different amino group on the protein or that it places a positive charge on the active amino group and thereby preserves enzymatic activity. In any case, applicants reacted 2-iminothiolane with barley hemitoxin at several reagent: protein ratios, separated the protein from unreacted 2-iminothiolane by gel exclusion chromatography on Sephadex G-25 and quantitated the amount of sulfhydryl groups introduced onto the hemitoxin by sulfhydryl exchange with the reactive, chromogenic disulfide. 5,5'-dithiobis (2-nitrobenzoic acid) (DTNB). The derivatized barley hemitoxin preparations were assayed for their ability to inhibit protein synthesis in ascites cell-free extracts and were found to have retained full activity.

FIG. 4 depicts inhibition of protein synthesis by 2-iminothiolane-conjugated barley hemitoxin. Barley hemitoxin was incubated at 0° C. for 90 minutes with 0 (o), 8-fold (x) or 24-fold (o) molar excess of 2-iminothiolane. The derivatized hemitoxins were then assayed for their ability to inhibit protein synthesis in ascites cell-free extracts. Proteins contained 0 (o), 0.76 (x) and 1.44 (o) moles of 2-iminothiolane bound per mole of hemitoxin.

Conjugation between the barley hemitoxin and [D-Lys$^6$, des-Gly$^{10}$]-GnRH-ethylamide was carried out by disulfide exchange. A sulfhydryl group was introduced into [D-Lys$^6$, des-Gly$^{10}$]-GnRH-ethylamide by reacting the hormone with a 16- fold molar excess of 2-iminothiolane at 0° C. for 2 hours. Derivatized [D-Lys$^6$, des-Gly$^{10}$]-GnRH-ethylamide was separated from unreacted 2-iminothiolane by chromatography on a Bio-Gel P-2 column equilibrated with 30% acetic acid. Acetic acid was removed from the isolated hormone by rotary evaporation followed by lyophilization. A reactive disulfide was prepared from barley hemitoxin as described above by incubating the hemitoxin with a 24-fold molar excess of 2-iminothiolane, isolating the protein and reacting it with DTNB to prepare the disulfide, and separating the hemitoxin from unreacted DTNB by column chromatography on Sephadex G-25. A 12-fold molar excess of derivatized [D-Lys$^6$, des-Gly$^{10}$]-GnRH-ethylamide was added to hemitoxin disulfide and disulfide exchange permitted to occur overnight at 4° C. Hemitoxin was separated from unconjugated GnRH by Sephadex G-25 column chromatography.

The reaction products were analyzed by SDS-polyacrylamide gel electrophoresis under non-reducing conditions. Analysis showed that the coupling reaction had converted approximately 50% of the 29 kDa barley hemitoxin (track 5) into a 31 kDa product (tracks 1–4) corresponding to a 1:1 hemitoxin-[D-Lys$^6$, des-Gly$^{10}$]-GnRH-ethylamide conjugate. The faint band of unreacted [D-Lys$^6$, des-Gly$^{10}$]-GnRH-ethylamide that can be seen in track 1 migrating ahead of the 14 kDa marker disappeared following acetone precipitation of the hemitoxin (track 2) or gel exclusion chromatography on Sephadex G-25 (tracks 3 & 4). The mixture of conjugate and unreacted hemitoxin was not purified further but was assayed directly for pituitary cell binding and killing.

Figure 4A:
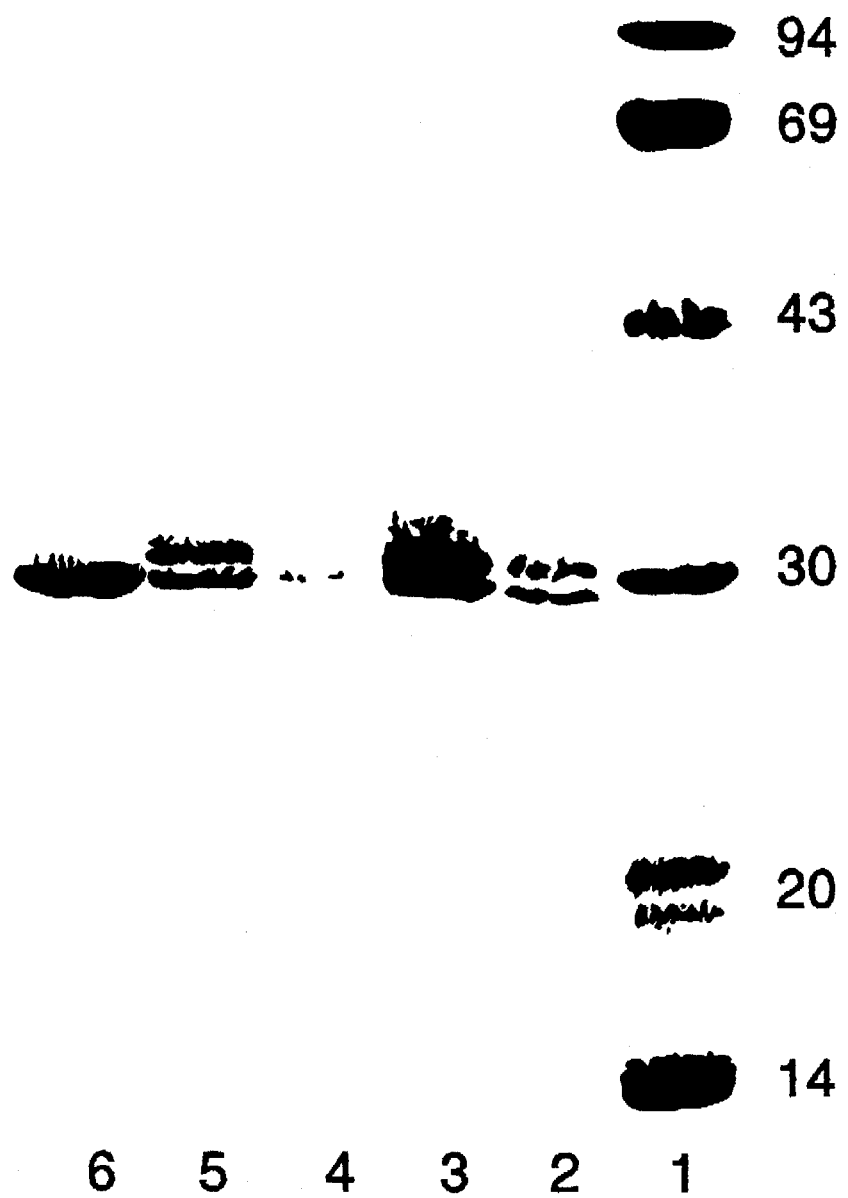

FIG. 4A depicts SDS-PAGE analysis of barley hemitoxin after conjugation to [D-Lys$^6$, des-Gly$^{10}$]-GnRH-ethylamide using 2-iminothiolane. Reaction products were analyzed before (tracks 1 & 2) and after tracks 3 & 4) Sephadex G-25 chromatography, and before (tracks 1 & 3) and after (tracks 2 & 4) concentrating by acetone precipitation. Track 5 contained unreacted hemitoxin.

Figure 5:
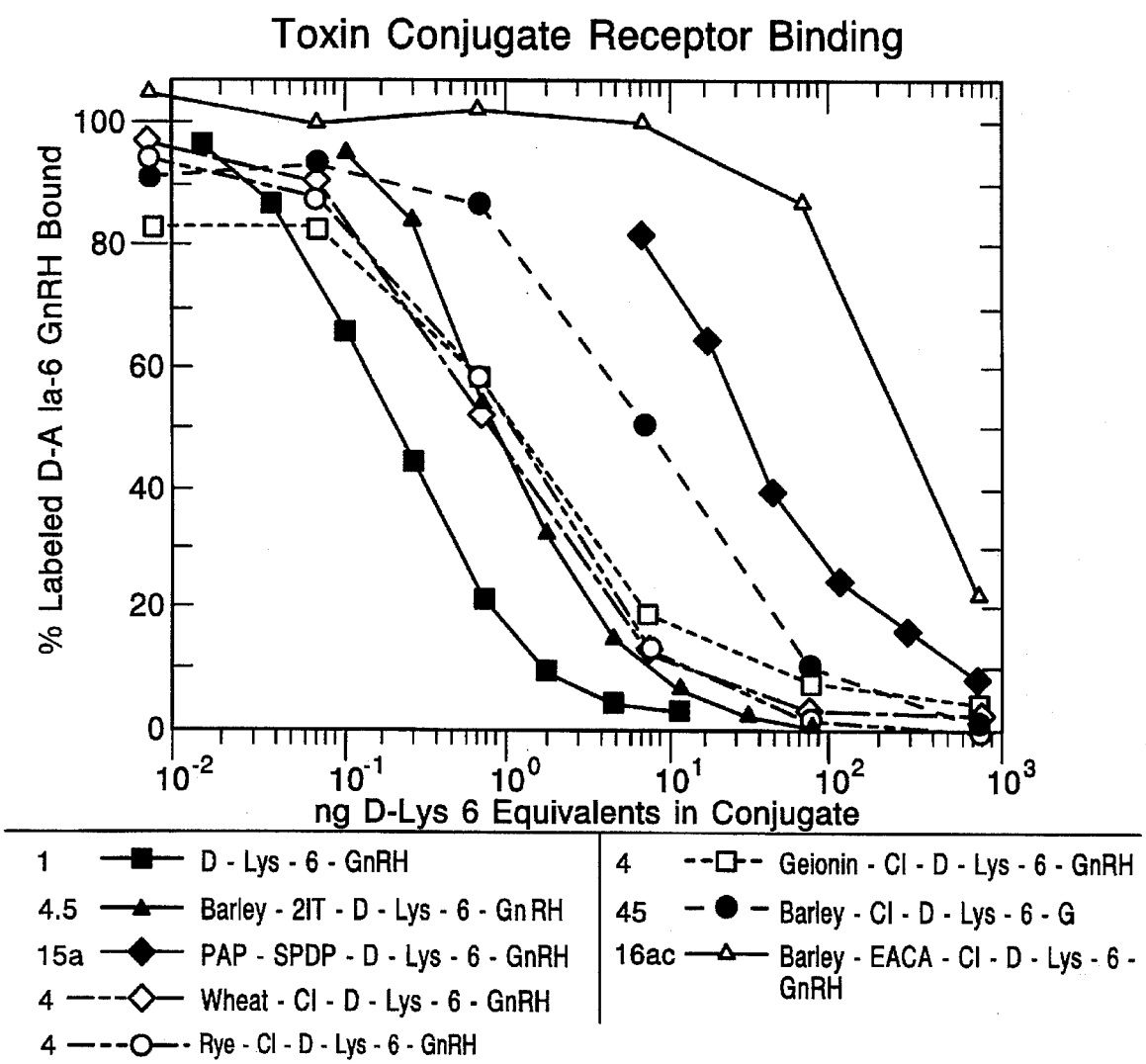

6. Conjugate Binding Studies. In order to assess whether [D-Lys$^6$, des-Gly$^{10}$]-GnRH-ethylamide toxin conjugates retain their ability to bind to receptors, the following assay was devised. Various concentrations of each conjugate were evaluated for their ability to displace 50,000 cpm $^{125}$I-D Ala$^6$-GnRH-ethylamide from bovine pituitary membranes. After incubation for 4 hours in standard conditions at 4° C., membranes were pelleted, counted in a gamma counter to determine the bound labelled ligand, and the ability of each conjugate to displace 50% of the label (IC$_{50}$ for unlabelled [D-Lys$^6$, des-Gly$^{10}$]-GnRH-ethylamide. FIG. 5 indicates the results of binding curves obtained in these experiments. Also shown are the calculated number of molecules required to displace 1 molecule of unconjugated [D-Lys$^6$, des-Gly$^{10}$]-GnRH-ethylamide. For example, FIG. 5 shows competitive binding of toxin conjugates to bovine pituitary membranes. The abbreviations are: 2IT, 2-iminothiolane; PAP, Pokeweed Antiviral Protein; SPDP, N-succinimidyl 3-(2-pyridyldithio) propionate; CI, Carbodiimide; EACA, Epsilon-amino caproic acid linker. Grain names refer to the purified hemitoxin source.

The data in FIG. 5 was critical in determining applicants' next steps. Several conclusions were reached. First, SPDP severely limits toxin activity (see FIG. 2). It also produces conjugates with greatly reduced binding activity (compare PAP-SPDP with Barley carbodiimide). On the other hand, use of carbodiimide produced conjugates with 3–40 fold improved binding compared to SPDP. However, there were differences among the hemitoxins used. For example, the wheat, rye and gelonin carbodiimide conjugates all showed greater binding than did the barley carbodiimide conjugate. However, the barley carbodiimide conjugate retained greater toxicity than the other grain hemitoxin conjugates in the cell free protein synthesis assay (data not shown). In this case, use of a spacer arm actually decreased binding affinity. Finally, the 2-iminothiolane conjugate made with barley hemitoxin as described above retained both 100% toxicity in the cell free system (see generally FIG. 4) and was as active as the best of the carbodiimide conjugates in binding. Applicants noted a 4.5 fold reduction in binding compared to the unconjugated [D-$Lys^6$, $desGly^{10}$]-GnRH-ethylamide. This was quite acceptable since native GnRH has also only about 1/30 the binding activity as this analogue (data not shown). Thus, after this exploratory work was completed, applicants carried out most further work with either the PAP-SPDP-[D-$Lys^6$, $desGly^{10}$]-GnRH-ethylamide or the barley 2-imminothiolane [D-$Lys^6$, $desGly^{10}$]-GnRH-ethylamide conjugate.

In Vitro Experiments.

The effect of these compounds on ovine pituitary cells in suspension culture was measured. A pituitary was removed from a ewe, sliced thinly, and dissociated with a mix of collagenase, hyaluronidase, and DNAase. The cells were washed several times and resuspended in culture medium containing 30% ram's serum. Cells were cultured in a 37° shaking water bath in 50 ml flasks under 95% $O_2$/5% $CO_2$. In a typical experiment, cells were divided into four groups after dissociation and cultured overnight (20 hr) with 1) culture medium only, 2) $10^{-8}$M GnRH, 3) $3\times10^{-9}$M Toxin-[D-$Lys^6$, $desGly^{10}$]-GnRH-ethylamide (molarity expressed in terms of GnRH receptor binding activity) and 4) Toxin at the same concentration as Toxin-[D-$Lys^6$, $desGly^{10}$]-GnRH-ethylamide. After pretreatment, the cells were washed 6 times, counted, and small aliquots removed for testing. The remainder were cultured in plain medium for 24 hours. To test the cells, aliquots of 500,000 cells were washed and resuspended in challenge medium containing $10^{-7}$M GnRH for 2 hours at 37° C. 3 ml of cold Gel-PBS was added to each tube, cells were centrifuged, and the media was measured for LH content. The four pretreatment groups were evaluated for their ability to synthesize and secrete LH immediately after treatment and after the 24 hour recovery period. The results of one experiment are shown in Table III.

TABLE III

| LH Synthesis and Release by Ovine Pituitary Cells (ng per 5 × $10^6$ cells) | |
|---|---|
| TREATMENT[1] | SYNTHESIS[2] |
| CONTROL | 526.3 |
| $10^{-8}$M GnRH | 545.5 |
| PAP | 137 |
| PAP-D-$Lys^6$ | 0 |

[1]Cells were incubated with the various treatments for 16 hours.
[2]Synthesis of LH was measured during a 24 hour period of culture after the agents were removed from the cells.

These data, although obtained with the least promising of our conjugates, reveal a large and specific effect of PAP-SPDP-[D-$Lys^6$, $desGly^{10}$]-GnRH-ethylamide (ethylamide is abbreviated as "EA" in Table III) on the gonadotropes ability to synthesize and secrete LH. It is not possible to determine whether the gonadotropes were specifically killed as they comprise <10% of the total number of pituitary cells, but the data strongly suggest the conjugate disrupted their normal function.

Applicants then tested the more promising Barley-2IT-[D-$Lys^6$, $desGly^{10}$]-GnRH-ethylamide conjugate in similar assay systems. Table IV shows the results of a similar experiment. Ovine pituitary cells were again placed in culture with various agents and the total LH in the cells and media determined after a 24 hour exposure, wash, and further 24 hour culture in standard media.

TABLE IV

| Total Culture LH after Exposure to GnRH and Toxin Conjugates with or without Lysosomal Agents | |
|---|---|
| Incubation Condition | Total LH (Ng/$10^5$ cells in Culture) |
| Control | 1.90 |
| D-$Lys^6$GnRH—EA | 1.62 |
| Barley Toxin | 1.49 |
| Barley Toxin-2IT-D-$Lys^6$GnRH—EA | .91 |
| Barley Toxin-2IT-D-$Lys^6$GnRH—EA + Monensin | 1.83 |
| Barley Toxin-2IT-D-$Lys^6$GnRH—EA + Chloroquine | .62 |
| Barley Toxin-2IT-D-$Lys^6$GnRH—EA + $NH_4Cl$ | 1.33 |
| Barley Toxin-2IT-D-$Lys^6$GnRH—EA + Killed Adenovirus | 1.13 |

These results indicate a specific killing effect of the toxin conjugate after only 24 hours of exposure. The lysosomally active agents do not potentiate this effect with the exception of chloroguine. When such experiments are combined with secondary challenge by GnRH, it appears that few gonadotropes are able to synthesize new LH after exposure to the barley toxin conjugate (data not shown).

7. In vivo Experiments. Several experiments were done to determine the effects of the pokeweed toxin (PAP) -SPDP-[D-$Lys^6$ , $desGly^{10}$]-GnRH-ethylamide conjugate in adult Sprague Dawley rats. Groups of 5–7 rats were treated with 20 ng of analogue; 20 ng conjugate (receptor binding assay equivalents), saline, or a conjugate made from a protein of similar molecular weight to the pokeweed toxin (carbonic anhydrase or ovalbumin). The most effective time course was found to be weekly injections for 4 weeks. The effect of such treatment was monitored in several ways. The ability of the animals to respond to a GnRH analogue challenge by measuring LH and/or serum testosterone levels 30–90 minutes after injection was followed. No difference was found among the groups. This result might be expected, since inducible LH release in intact animals is quite small secondary to chronic feedback suppression by the testicular androgens. Secondly, applicants followed gonad weights and found the testes in the PAP-[D-$Lys^6$, $desGly^{10}$]-GnRH-ethylamide group to be decreased by 50%, although the control conjugates had similar effects. The PAP-[D-$Lys^6$, $desGly^{10}$]-GnRH and carbonic anhydrase conjugate groups were found to be infertile in breeding tests, indicating a potential effect of this enzyme on testis tissue. Interestingly, light microscopy of these animals revealed no changes in the pituitaries, but interstitial (Leydig) cell depletion in the PAP-SPDP-[D-$Lys^6$, $desGly^{10}$]-GnRH-ethylamide treated group, indicating a possible specific cellular effect on rat testicular function. This was not surprising since there are GnRH receptors on Leydig cells in the rat testis.

Applicants also tested the PAP-carbodiimide-[D-$Lys^6$, $desGly^{10}$]-GnRH-ethylamide conjugate in ovariectomized female rats. In contrast to the SPDP conjugate, and in this system where gonadal feedback is not a problem, this drug appears capable of producing a 15 fold decrease in the serum LH response to GnRH analogue challenge (FIG. 1A or 1B), again indicating the importance of applicant's studies on various linking techniques.

FIG. 1B indicates the results of a challenge by one of applicants' compounds to ovariectomized rats. Serum concentrations of LH in ovariectomized rats treated with saline (hatched bars) or pokeweed anti-viral protein conjugated to a GnRH super-agonist (solid bars) are depicted. The open space above the bars indicates the amount of LH released in response to a GnRH challenge. The challenges were administered on the first day of treatment and again 4 weeks later. Compared to control there was greater than a 90% reduction in LH release after GnRH challenge at 4 weeks of treatment.

Based on the above data (with regards to LH synthesis inhibition) applicants then carried out experiments in intact male and female rats. Animals received 4 injections at 3 day intervals of PAP-Cl-[D-Lys$^6$, desGly$^{10}$]-GnRH-ethylamide or of the GnRH analogue or toxin alone or saline. Conjugate treated male animals (but not control) showed a 50% reduction in fertility (i.e., 50% of females exposed to these male animals became pregnant, compared to 100% of controls). Histologic examination of the testes of experimental animals revealed residual spermatogenesis in about 10% of tubules. In conjugate treated female animals, fertility was abrogated for more than 4 months (time sufficient for about 30 reproductive cycles in normal animals) following treatment. There were no side effects noted from these injections.

To further understand the effect of hemitoxins and conjugates on non-target tissues, applicants initiated studies on the tissue distribution of $^{125}$I-toxin-conjugates and have demonstrated important differences among the toxins in (for example) concentration in the kidneys, indicating the importance of testing the various proteins to avoid potential non-target tissue toxicity. For example, applicants have found that the tissue/serum ratio of unconjugated PAP 2 hours after injection for various organs ranges from 0.03 in brain to 85.5 in kidney. In contrast, unconjugated barley hemitoxin is 8-fold less concentrated in kidney (see Table IV). Conjugation with the GnRH analogue alters these ratios considerably.

TABLE V

| Tissue | Tissue Distribution of Hemitoxins and Hemitoxin Conjugates | |
|---|---|---|
| | PAP | PAP-SPDP-D-Lys$^6$GnRH |
| Pituitary | .20 | .11 |
| Brain | .03 | .01 |
| Adrenal | .48 | .02 |
| Kidney | 85.5 | 12.6 |
| Liver | 2.48 | 1.07 |
| Spleen | 2.29 | .73 |
| Testis | .03 | .02 |

| | Tissue/serum Ratio of Labeled Protein | |
|---|---|---|
| GnRH | Barley | Barley-Cl-D-Lys$^6$GnRH |
| Pituitary | 1.08 | 1.06 |
| Brain | .04 | .04 |
| Adrenal | .70 | 1.5 |
| Kidney | 10.5 | 4.0 |
| Liver | .43 | 3.52 |
| Spleen | .4 | 5.07 |
| Testis | .10 | .10 |

Thus these experiments produced a group of compounds capable of sterilizing (temporarily or permanently) animals by destroying the gonadotrophs of an animal's anterior pituitary gland. These compounds can be administered in the form of pharmaceutically acceptable, and otherwise non-toxic salts. It should also be noted that these compounds can be administered individually, or in combination with each other, to animals intravenously, subcutaneously, intramuscularly or orally to achieve fertility inhibition and/or control. Preferably administration will be intravenous or intramuscular in a suitable carrier such as, for example, in isotonic saline phosphate buffer solutions or the like. They also can be used in applications calling for reversible suppression of gonadal activity, such as for the management of precocious puberty or during radiation or chemotherapy. Effective dosages will vary with the form of administration and the particular species of mammal being treated. An example of one typical dosage form is a physiological saline solution containing the peptide which solution is administered to provide a dose in the range of about 0.1 to 10 mg/kg of body weight.

Although the invention has been described with regard to its preferred embodiments, it will be apparent to those skilled in this art, upon reading the above, detailed description and examples, that various modifications and extensions can be made thereto without departing from the spirit of the present invention and that the scope of said invention shall be limited only by the scope of the appended claims.

Thus having disclosed this invention, what is claimed is:

1. A method for functionally inactivating gonadotrophs in the pituitary gland of an animal, comprising administering to said animal an effective amount of a hormone/toxin conjugate comprising a peptide hormone conjugated to a toxin group, wherein said conjugate is capable of selectively binding with receptors on said gonadotrophs to render said gonadotrophs essentially incapable of secreting gonadotropins, wherein said animal is not weakened or killed by said method.

2. A method of claim 1, wherein said method is effective to temporarily sterilize said animal.

3. A method of claim 1, wherein said method effects permanent sterilization of said animal.

4. A method of claim 1, wherein said method is effective for treating a sex hormone related disease in said animal.

5. A method of claim 1, wherein said peptide hormone is GnRH or an analog thereof.

6. A method of claim 1, wherein said peptide hormone has the general formula

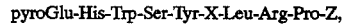

pyroGlu-His-Trp-Ser-Tyr-X-Leu-Arg-Pro-Z, wherein X is an amino acid selected from the group consisting of lysine, D-lysine, ornithine, D-ornithine, glutamic acid, D-glutamic acid, aspartic acid, D-aspartic acid, cysteine, D-cysteine, tyrosine and D-tyrosine; and Z is a substituent selected from the group consisting of Gly-NH$_2$, ethylamide, and AzA-Gly-NH$_2$.

7. A method of claim 1, wherein said peptide hormone comprises [D-Lys$^6$-des-Gly$^{10}$]-GnRH-ethylamide.

8. A method of claim 1, wherein said toxin group is a modified toxin comprising a toxic domain and a translocation domain but lacking a functional toxin cell binding domain.

9. A method of claim 1, wherein said toxin group is a toxin selected from the group consisting of a chemical toxin, a single chain toxin, and a modified toxin having an intrinsic toxic group and intrinsic translocation domain but lacking a functional intrinsic toxin cell binding domain.

10. A method of claim 9, wherein said modified toxin is selected from the group consisting of modified ricin toxins, modified modeccin toxins, modified abrin toxins, modified diphtheria toxins, modified Pseudomonas exotoxins and modified shiga toxins.

11. A method of claim 9, wherein said single chain toxin is selected from the group consisting of pokeweed antiviral protein, α-amanitin, gelonin ribosome inhibiting protein ("RIP"), barley RIP, wheat RIP, corn RIP, rye RIP, flax RIP, and modified forms thereof.

12. A method of claim 9, wherein said chemical toxin is selected from the group consisting of melphalan, methotrexate, nitrogen mustard, doxorubicin and daunomycin.

13. A method of claim 1, wherein said toxin group is selected from the group consisting of modified diphtheria toxins and modified Pseudomonas exotoxins, wherein said toxin group comprises a toxic domain and a translocation domain but lacks a functional toxin cell binding domain.

14. A method of claim 1, wherein said peptide hormone is conjugated to said toxin group using a linking agent capable of forming a stable conjugate that does not substantially degrade prior to binding with said gonadotrophs but which is capable of releasing a sufficient amount of said toxin group from said conjugate in the cytosol of said gonadotrophs to substantially preclude secretion of gonadotropins by said gonadotrophs.

15. A method of claim 14, wherein said linking agent is selected from the group consisting of 2-iminothiolane, N-succinimidyl-3-(2-pyridyldithio) propionate (SPDP), 4-succinimidyloxycarbonyl-α-(2-pyridyldithio)toluene (SMPT), m-maleimidobenzoyl-N-hydroxysuccinimide ester (MBS), N-succinimidyl(4-iodoacetyl)aminobenzoate (SIAB), succinimidyl 4-(p-maleimidophenyl)butyrate (SMPB), 1-ethyl-3-(3-dimethylaminopropyl)carbodiimide (EDC), bis-diazobenzidine and glutaraldehyde.

16. A method of claim 14, wherein said linking agent is selected from the group consisting of SMPB, 2-iminothiolane, and EDC.

17. A method of claim 1, further comprising challenging said animal with GnRH at least about four weeks after said step of administering said conjugate to said animal, said challenging not inducing substantial secretion of luteinizing hormone by said animal.

18. A method of claim 1, wherein said method of administering said conjugate is repeated at least once over a time period such that administration of said conjugate does not elicit a substantial production of antibodies against said conjugate.

19. A method of claim 1, wherein said conjugate has the general formula pyroGlu—His—Trp—Ser—Tyr—D-Lys—Leu—Arg—Pro-ethylamide
                              |
                              Y
                              |
                              T wherein Y comprises SMPB and wherein T is a toxin group selected from the group consisting of modified diphtheria toxins and modified Pseudomonas exotoxins, wherein said toxin group comprises a toxic domain and a translocation domain but lacks a functional toxin cell binding domain.

20. The method of claim 19, wherein said sex hormone related disease is selected from the group consisting of breast cancer, prostate cancer, pancreatic cancer, and endometriosis.

21. The method of claim 1, wherein said conjugate can interact with GnRH receptors and gain entry into cells presenting said receptors.

22. A method for chemically attacking cells whose membranes contain receptors for GnRH, comprising administering to an animal an effective amount of a hormone/toxin conjugate comprising a peptide hormone that is capable of binding to a GnRH receptor, said peptide hormone conjugated to a toxin group, wherein said conjugate is capable of selectively binding to said GnRH receptors on said cells.

23. The method of claim 22, wherein said peptide hormone is GnRH or an analog thereof.

24. The method of claim 22, wherein said peptide hormone has the general formula pyroGlu-His-Trp-Ser-Tyr-X-Leu-Arg-Pro-Z, wherein X is an amino acid selected from the group consisting of lysine, D-lysine, ornithine, D-ornithine, glutamic acid, D-glutamic acid, aspartic acid, D-aspartic acid, cysteine, D-cysteine, tyrosine and D-tyrosine; and Z is a substituent selected from the group consisting of Gly-NH$_2$, ethylamide, and AzA-Gly-NH$_2$.

25. The method of claim 22, wherein said toxin group is a modified toxin comprising a toxic domain and a translocation domain but lacking a functional toxin cell binding domain.

26. The method of claim 22, wherein said toxin group is a toxin selected from the group consisting of a chemical toxin, a single chain toxin, and a modified toxin having an intrinsic toxic group and intrinsic translocation domain but lacking a functional intrinsic toxin cell binding domain.

27. The method of claim 22, wherein said conjugate has the general formula pyroGlu—His—Trp—Ser—Tyr—D-Lys—Leu—Arg—Pro-ethylamide
                              |
                              Y
                              |
                              T wherein Y comprises SMPB and wherein T is a toxin group selected from the group consisting of modified diphtheria toxins and modified Pseudomonas exotoxins, wherein said toxin group comprises a toxic domain and a translocation domain but lacks a functional toxin cell binding domain.

* * * * *